(12) United States Patent
Fossey et al.

(10) Patent No.: US 6,292,259 B1
(45) Date of Patent: Sep. 18, 2001

(54) WAFER INSPECTION SYSTEM FOR DISTINGUISHING PITS AND PARTICLES

(75) Inventors: Michael E. Fossey; John C. Stover, both of Charlotte, NC (US)

(73) Assignee: ADE Optical Systems Corporation, Charlotte, NC (US)

( * ) Notice: Subject to any disclaimer, the term of this patent is extended or adjusted under 35 U.S.C. 154(b) by 0 days.

(21) Appl. No.: 09/624,502

(22) Filed: Jul. 24, 2000

Related U.S. Application Data

(63) Continuation of application No. 08/958,230, filed on Oct. 27, 1997, now Pat. No. 6,118,525, which is a continuation-in-part of application No. 08/399,962, filed on Mar. 6, 1995, now Pat. No. 5,712,701.
(60) Provisional application No. 60/032,103, filed on Dec. 4, 1996.

(51) Int. Cl.$^7$ .................................................. G01N 21/00
(52) U.S. Cl. .................. 356/237.2; 356/343; 356/364; 356/237.4
(58) Field of Search .............................. 356/237.2, 237, 356/364, 430, 394, 338, 343; 250/559.18, 559.39–559.41, 559.44–559.46, 225

(56) References Cited

U.S. PATENT DOCUMENTS

| 3,749,496 | 7/1973 | Hietanen et al. . |
| 3,904,293 | 9/1975 | Gee . |
| 4,297,032 | 10/1981 | Temple . |
| 4,314,763 | 2/1982 | Steigmeier et al. . |
| 4,441,124 | 4/1984 | Heebner et al. . |

(List continued on next page.)

FOREIGN PATENT DOCUMENTS

| 42 27 593A | 2/1993 | (DE) . |
| 2 321 964A | 8/1988 | (GB) . |
| 61-240663 | 10/1986 | (JP) . |
| 2-216035 | 8/1990 | (JP) . |
| 3-128445 | 5/1991 | (JP) . |
| 5-1889 | 1/1993 | (JP) . |
| 5-118994 | 5/1993 | (JP) . |
| 5-142156 | 6/1993 | (JP) . |
| 5-288536 | 11/1993 | (JP) . |
| 6-174655 | 6/1994 | (JP) . |

(List continued on next page.)

OTHER PUBLICATIONS

Bawolek, "Light Scattering by Spherial Particles on Semiconductor Surfaces," 1992 Ph.D. Dissertation at Arizona State University, pp. I–281.

Starr et al., "Comparison of Experimentally Measured Differential Scattering Cross Sections of PSL Spheres on Flat Surfaces and patterned Surfaces," SPIE vol. 2862, (Sep. 1996) pp. 130–138.

Wolfe et al., "A Portable Scatterometer for Optical Shop Use," SPIE vol. 675 (1986) pp. 160–165.

(List continued on next page.)

Primary Examiner—Frank G. Font
Assistant Examiner—Layla Lauchman
(74) Attorney, Agent, or Firm—Fish & Richardson, P.C.

(57) ABSTRACT

A surface inspection system and method is provided which detects defects such as particles or pits on the surface of a workpiece, such as a silicon wafer, and also distinguishes between pit defects and particle defects. The surface inspection system comprises an inspection station for receiving a workpiece and a scanner positioned and arranged to scan a surface of the workpiece at the inspection station. The scanner includes a light source arranged to project a beam of P-polarized light and a scanner positioned to scan the P-polarized light beam across the surface of the workpiece. The system further provides for detecting differences in the angular distribution of the light scattered from the workpiece and for distinguishing particle defects from pit defects based upon these differences.

42 Claims, 19 Drawing Sheets

U.S. PATENT DOCUMENTS

| | | |
|---|---|---|
| 4,448,527 | 5/1984 | Reich . |
| 4,469,442 | 9/1984 | Reich . |
| 4,505,585 | 3/1985 | Ohshima et al. . |
| 4,508,450 | 4/1985 | Ohshima et al. . |
| 4,541,712 | 9/1985 | Whitney . |
| 4,630,276 | 12/1986 | Moran . |
| 4,740,708 | 4/1988 | Batchelder . |
| 4,764,017 | 8/1988 | Hirvonen . |
| 4,794,264 | 12/1988 | Quackenbos et al. . |
| 4,794,265 | 12/1988 | Quackenbos et al. . |
| 4,875,780 | 10/1989 | Moran . |
| 4,889,998 | 12/1989 | Hayano et al. . |
| 4,893,932 | 1/1990 | Knollenberg . |
| 4,898,471 | 2/1990 | Stonestrom et al. . |
| 4,902,131 | 2/1990 | Hayano et al. . |
| 4,922,308 | 5/1990 | Noguchi et al. . |
| 4,933,567 | 6/1990 | Silva et al. . |
| 4,966,457 | 10/1990 | Hayano et al. . |
| 4,991,445 | 2/1991 | Forgey et al. . |
| 4,991,964 | 2/1991 | Forgey et al. . |
| 5,030,842 | 7/1991 | Koshinaka et al. . |
| 5,032,734 | 7/1991 | Orazio et al. . |
| 5,067,798 | 11/1991 | Tomoyasu . |
| 5,108,176 | 4/1992 | Malin et al. . |
| 5,125,741 | 6/1992 | Okada et al. . |
| 5,127,726 | 7/1992 | Moran . |
| 5,177,559 | 1/1993 | Batchelder et al. . |
| 5,189,481 | 2/1993 | Jann et al. . |
| 5,191,466 | 3/1993 | Gross et al. . |
| 5,355,212 | 10/1994 | Wells et al. . |
| 5,363,187 * | 11/1994 | Hagiwara et al. ............... 356/237.3 |
| 5,369,286 | 11/1994 | Cheng . |
| 5,389,794 | 2/1995 | Allen et al. . |
| 5,424,536 | 6/1995 | Moriya . |
| 5,436,464 * | 7/1995 | Hayano et al. ...................... 356/237 |
| 5,461,474 | 10/1995 | Yoshii et al. . |
| 5,465,145 * | 11/1995 | Nakashige et al. .................. 356/237 |
| 5,486,919 * | 1/1996 | Tsuji et al. ............................ 356/237 |
| 5,585,916 * | 12/1996 | Miura et al. .......................... 356/237 |
| 5,625,193 * | 4/1997 | Broude et al. .................. 250/559.18 |
| 5,712,701 | 4/1996 | Clementi et al. . |
| 5,717,485 | 2/1998 | Ito et al. . |
| 5,798,829 | 8/1998 | Vaez-Iravani . |
| 5,883,710 | 3/1999 | Nikoonahad et al. . |
| 5,903,342 * | 5/1999 | Yatsugake et al. ............... 356/237.4 |
| 5,936,726 * | 8/1999 | Takeda et al. .................... 356/237.2 |
| 6,081,325 | 6/2000 | Leslie et al. . |
| 6,104,481 * | 8/2000 | Sekine et al. ..................... 356/237.5 |

FOREIGN PATENT DOCUMENTS

| | | |
|---|---|---|
| 06229939 | 8/1994 | (JP) . |
| 6-242015 | 9/1994 | (JP) . |
| 07146245 | 6/1995 | (JP) . |
| 071462454 | 6/1995 | (JP) . |
| 7-81958 | 9/1995 | (JP) . |
| 07270326 | 10/1995 | (JP) . |
| 7-318504 | 12/1995 | (JP) . |
| 09145630 | 6/1997 | (JP) . |
| 2661913 | 6/1997 | (JP) . |
| 09210918 | 8/1997 | (JP) . |
| 2747921 | 2/1998 | (JP) . |
| 10-221268 | 8/1998 | (JP) . |
| 10-282009 | 10/1998 | (JP) . |
| 10-510359 | 10/1998 | (JP) . |
| 096987 | 3/1988 | (TW) . |
| 94/12867 | 6/1994 | (WO) . |
| 96/18094 | 6/1996 | (WO) . |
| WO 96/28721 | 9/1996 | (WO) . |
| WO 97/46865 | 9/1996 | (WO) . |
| WO 97/12226 | 4/1997 | (WO) . |
| WO 99/14574 | 3/1999 | (WO) . |

OTHER PUBLICATIONS

Magee et al., "Near–specular Performance of a Portable Scatterometer," SPIE vol. 675 (1986) pp. 249–259.

Bickel et al., "The Role of Polarized in the Measurement and Characterization of Scattering," SPIE vol. 679 (1986) pp. 91–98.

Iafelice et al., "Polarized Light–Scattering Matrix Elements for Select Perfect and Pertubed Optical Surfaces," Applied Optics 26(12) (1987) pp. 2410–2415.

Bickel et al., "Strokes Vectors, Mueller Matrices and Polarized Scattered Light: Experimental Applications to Optical Surfaces and All Other Scatters, " SPIE vol. 1530 (1991) pp. 7–14.

Bickel et al. "Polarized Light Scattering from Metal Surfaces," J. of Applied Physics 61 (12) (1987) pp. 5392–5398.

Kylner et al., "Scattering Signatures of Isolated Surfaces Features," SPIE vol. 1995 (1993) pp. 66–72.

TMA Technologies, "TMA QuikScan®Scatterometer," (1991) Brochure, 4 pages.

"Manufacturing: Scatterometers Improve Lasers Mirrors," POTONICS SPECTRA vol. 25, Issue 8 (Aug. 1991) p. 100.

Rifkin et al., "Design Review of a Comlete Angle Scatter Instruments," SPIE vol. 1036 (1988) pp. 116–124.

Stover et al., "Optical Scattering Measurement and Analysis," (1995) Second Edition.

Wagner et al., "Requirement of Future Measurement Equipment for Silicon Wafers," SPIE vol. 2862 (Sep. 1996) pp. 152–162.

Nebeker, "Modeling of Light Scattering from Structures with Particle Contaminants," SPIE vol. 2862 (Sep. 1996) pp. 139–150.

Stover et al. "Measurement and Analysis of Scatter from Silicon Wafers," SPIE vol. 2260 (1994) pp. 182–191.

Stover et al., "Some Deviations Associated with Vector Pertubation Diffraction Theory," SPIE vol. 511 (1984) pp. 12–17.

Sasse, "Angular Scattering Measurement and Calculations of Rough Spherically Shaped Carbon Particles" SPIE vol. 2541 (1995) pp. 131–139.

Nee, "Reflection, Scattering, and Polarization from a Very Rough Black Surface," SPIE vol. 1995 (1993) pp. 202–212.

Church et al., "Scattering by Anisotropic Grains in Beryllium Mirrors," SPIE vol. 1331 (1990) pp. 12–17.

Stover, Editor, "Optical Scattering: Applications, Measurement, and Theory II," vol. 1995 (1993), pp. 1–302.

Videen et al., "Polarized Light Scattered from Rough Surfaces," Opt. Soc. Am. vol. 9, No. 7 (1992), pp. 1111–1118.

* cited by examiner

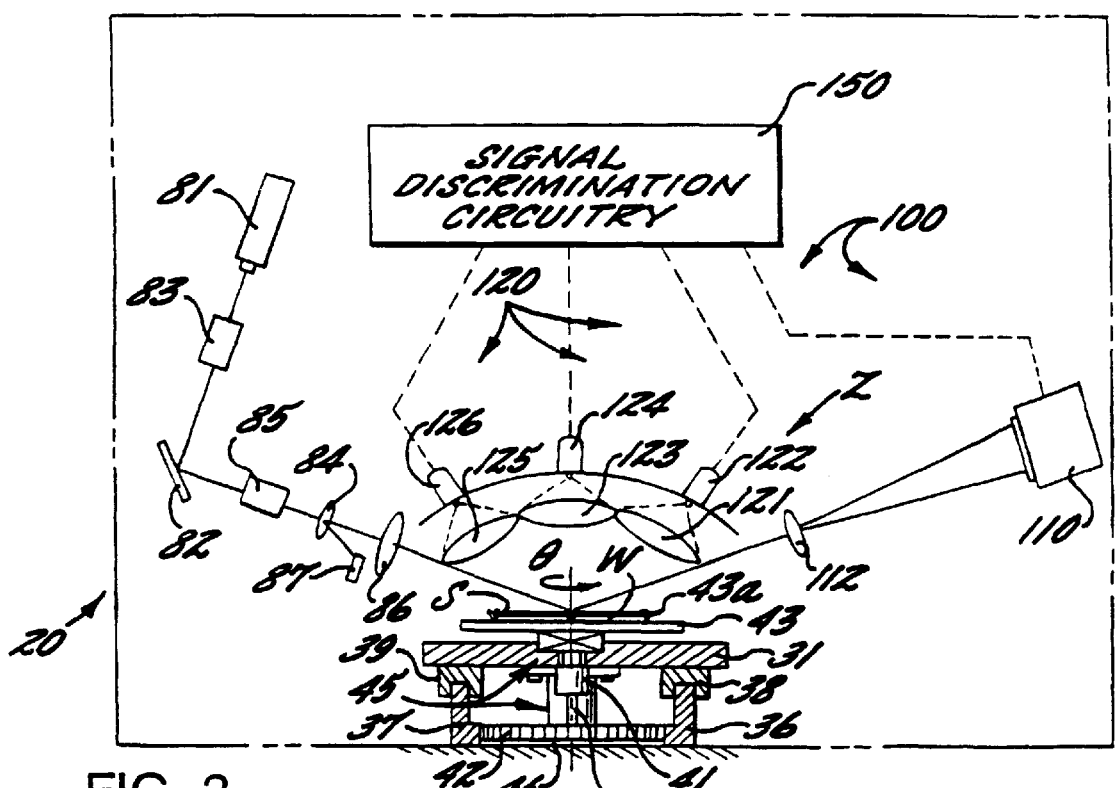
FIG. 3
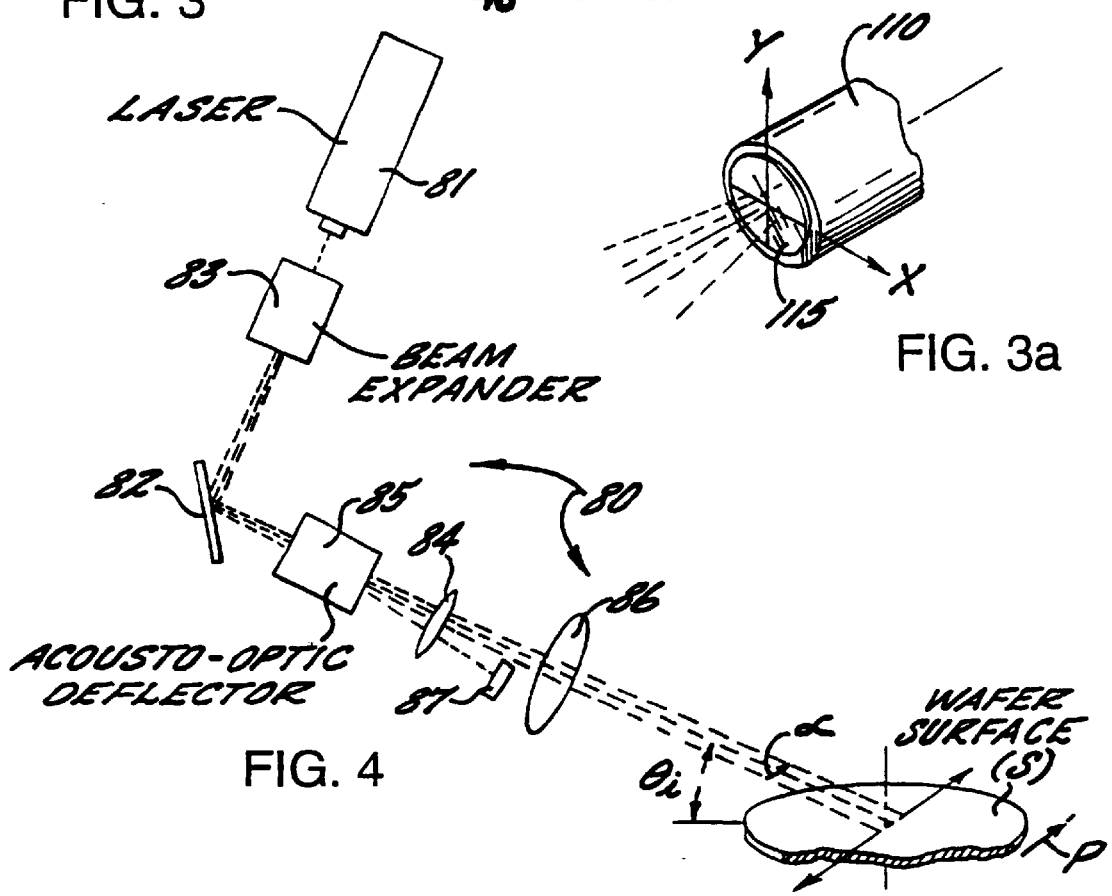
FIG. 3a
FIG. 4

WAFER INSPECTION SYSTEM FOR DISTINGUISHING PITS AND PARTICLES

CROSS REFERENCE TO RELATED APPLICATION

This application is a continuation of application Ser. No. 08/958,230, filed Oct. 27, 1997, now U.S. Pat. No. 6,118, 525, which claims benefit of Provisional No. 60/032,103, Dec. 4, 1996 which is a continuation-in-part of application Ser. No. 08/399,962, filed Mar. 6, 1995, now U.S. Pat. No. 5,712,701.

FIELD AND BACKGROUND OF THE INVENTION

The present invention relates to surface inspection systems and methods and, more particularly, to the inspection of articles or workpieces, such as silicon wafers, to detect the presence of defects such as particles or pits on the surface and to distinguish therebetween.

Surface inspection systems are commonly used for the inspection of articles or workpieces such as silicon wafers to detect the presence of defects on the wafer surface. When the inspection indicates a large number of defects, the wafer may be sent back for recleaning. If the defects are particles or other debris on the wafer surface, the recleaning is successful. However, if the defects are pits or "COPS" (crystal originated pits) in the wafer surface, they are not removed by recleaning. Because such surface inspection systems fail to distinguish between pit defects and particle defects, the wafer is typically sent back for recleaning regardless of whether the defects are pits or particles. Because these defects may be pits, recleaning the wafer may result in nothing more than a waste of time and resources. It would be advantageous to be able to distinguish pits in the surface of the wafer from particles located thereon.

SUMMARY OF THE INVENTION

The present invention provides a surface inspection system and method which not only detects defects such as particles or pits on the surface of a workpiece, such as a silicon wafer, but also distinguishes between pit defects and particle defects. This makes it possible to easily ascertain whether the workpiece requires recleaning to remove particle defects, or whether other measures must be taken.

In a broad aspect, the surface inspection system comprises an inspection station for receiving a workpiece and a scanner positioned and arranged to scan a surface of the workpiece at said inspection station. The scanner includes a light source arranged to project a beam of P-polarized light and a scanner positioned to scan the P-polarized light beam across the surface of the workpiece. The system further provides for detecting differences in the angular distribution of the light scattered from the workpiece and for distinguishing particle defects from pit defects based upon these differences. The differences in the angular distribution of the scattered light may, for example, be detected by comparing the amount of light scattered in a direction substantially perpendicular from the surface of the workpiece to the amount of light backscattered from the surface of the workpiece The detection of differences in the angular distribution of the scattered light may also, for example, involve identifying a dip in the intensity distribution of the scattered light.

The scanner preferably scans across the surface of the workpiece along a relatively narrow scan path during rotational and translational travel of the workpiece. More specifically, the system preferably has a transporter arranged for transporting the workpiece along a material path and a rotator associated with the transporter and arranged for rotating the workpiece during translational travel along the material path. The scanner is positioned and arranged for scanning a surface of a workpiece during rotational and translational travel along the material path so that the entire surface of the workpiece is raster scanned in a spiral pattern. The scanner includes either a P-polarized light source or a light source coupled with a P-polarized filter positionally aligned with the light source.

A collector also is arranged for collecting light reflected and scattered from the surface of the workpiece during rotational and translational travel along the material path. The collector includes a dark channel detector positioned for detecting light which is scattered from the surface of a workpiece. The dark channel detector includes a plurality of collectors positioned and arranged for collecting light at different angles relative to the surface of the workpiece. Each collector includes a photodetector for generating electrical signals in response to the collected light. The electrical signals from photodetectors located at the different angles are compared to determine the differences in angular distribution of the scattered light.

The plurality of collectors preferably includes a forward channel collector arranged to collect light components scattered forwardly from the surface of the workpiece at a relatively small angle with respect to the specular reflection from the workpiece, a center channel collector positioned adjacent to the forward channel collector and arranged to collect light components scattered substantially normal from the surface of the workpiece at a relatively medium angle, and a back channel collector positioned adjacent to the center channel collector and arranged to collect light components scattered backwardly from the surface of the workpiece at a relatively large angle.

When the scanned light beam contacts a defect, such as a pit or a particle, light is scattered from the surface and is collected by the collectors. The intensity of the scattered light, and the time of its detection during the scan, provide information about the size and location of the defect on the surface of the workpiece. Furthermore, the nature of the defect, i.e. whether it is a pit or a particle, can be ascertained by detecting differences in the angular distribution of the light scattered from the workpiece. For example, if the defect is a pit, the amount of light scattered and detected by the center channel collector is typically greater than that detected by the back channel collector. Alternatively, if the defect is a particle, the amount of the light detected by the center channel collector is typically less than that detected by the back channel collector and/or the forward channel collector. The dark channel collector system provides the surface inspection system of the present invention with high sensitivity to more readily identify, classify, and/or provide a topography of the condition of the surface of an article or a workpiece, including defects such as particles, pits and the like, in and on the surface of a workpiece.

According to one specific embodiment of the invention, a P-polarized light beam is directed along a predetermined relatively narrow scan path and at a relatively low angle of incidence with respect to the surface of the workpiece. The method preferably also includes imparting a rotational and translational movement of the workpiece during the narrow scan so that the narrow scan path traverses the entire surface of the workpiece along a spiral path.

The surface inspection system and method of the present invention advantageously distinguish pits in the surface of the wafer from particles on the surface of the wafer and therefore determine whether cleaning or some other course of action, e.g., altering the conditions of manufacture and storage, can be used to cure the defects. In addition, the surface inspection system and method provide high spatial resolution, a small field of view at the object plane which, in turn, provides improved edge detection performance, improved repeatability in the inspection process and reduces interference signals caused by scatter from air molecules.

BRIEF DESCRIPTION OF THE DRAWINGS

Other advantages will appear as the description proceeds when taken in connection with the accompanying drawings, in which:

FIG. 3 schematically illustrates a side elevational view of a surface inspection system according to the present invention.

FIG. 3A is a fragmentary view of a light channel detector of a surface inspection system according to the present invention.

FIG. 4 schematically illustrates a side elevational view of an optical scanning system of a surface inspection system according to the present invention.

DESCRIPTION OF ILLUSTRATED EMBODIMENT

The present invention will be described more fully hereinafter with reference to the accompanying drawings in which specific embodiments of the invention are shown. This invention may, however, be embodied in many different forms and should not be construed as limited to the illustrated embodiments set forth herein; rather, these illustrated embodiments are provided so that this disclosure will be thorough and complete and will fully convey the scope of the invention to those skilled in the art. Like numbers refer to like elements throughout.

Figure 1:
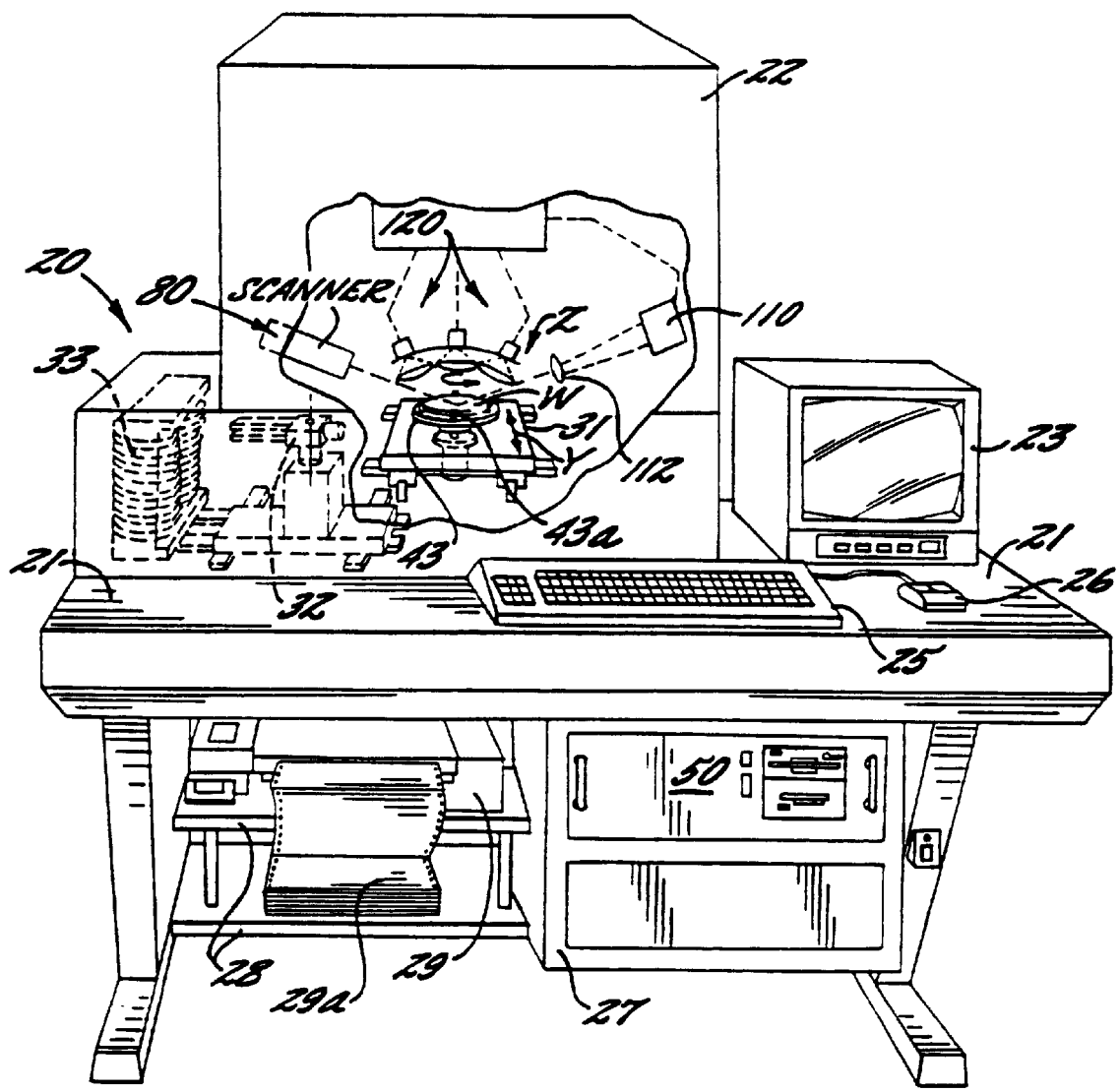
FIG. 1 is a perspective view of a surface inspection system according to the present invention.

FIG. 1 is a perspective view of a surface inspection system 20 for detecting defects such as particles, pits and the like on a surface of a workpiece W or article, such as a silicon wafer. Portions of the system 20 are broken away for purposes of clarity and shown by phantom lines to illustrate various elements of the surface inspection system 20. The surface inspection system 20 is suitably used for inspecting the surface of unpatterned wafers W, both with and without deposited films. The system 20 preferably includes means for translationally transporting a workpiece W along a material path P, means associated with the translational transporting means for rotating the workpiece W as it travels along the material path P, means for scanning the surface S of the workpiece W during rotative and translational travel along the material path P, and means for collecting light reflected and scattered from the surface S of the workpiece W.

As illustrated in FIG. 1, the surface inspection system 20 is arranged as a workstation including a worktable 21. Positioned on the worktable 21 is a generally closed and substantially light proof housing 22, a video display 23, a keyboard 25, and a mouse 26. A cabinet 27 is suspended from the worktable for carrying a system controller 50. Adjacent the cabinet 27 is a shelf unit 28 for carrying a printer 29 and associated printing paper 29a. The housing 22 has been partially broken away to better illustrate the inspecting arrangement of the present invention. The inspection of the wafer W preferably is conducted in an inspection zone Z on an inspection table 31. A robotic wafer handling device 32 is located adjacent the inspection station 20 to load and unload wafers W from a cassette 33 onto the table 31. The cassette 33 holds a number of wafers W and is loaded into the cabinet 27 through a door (not shown). The handling of the wafers W inside the housing 22 is done automatically without contact by human hands to avoid contamination or smudges.

Figure 2:
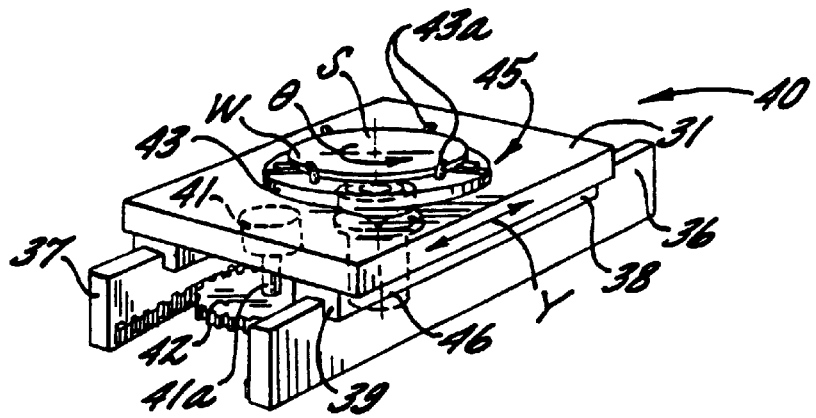
FIG. 2 illustrates a transporter of a surface inspection system according to the present invention arranged for rotatively and translationally transporting a workpiece, such as a wafer, along a material path.
Figure 5:
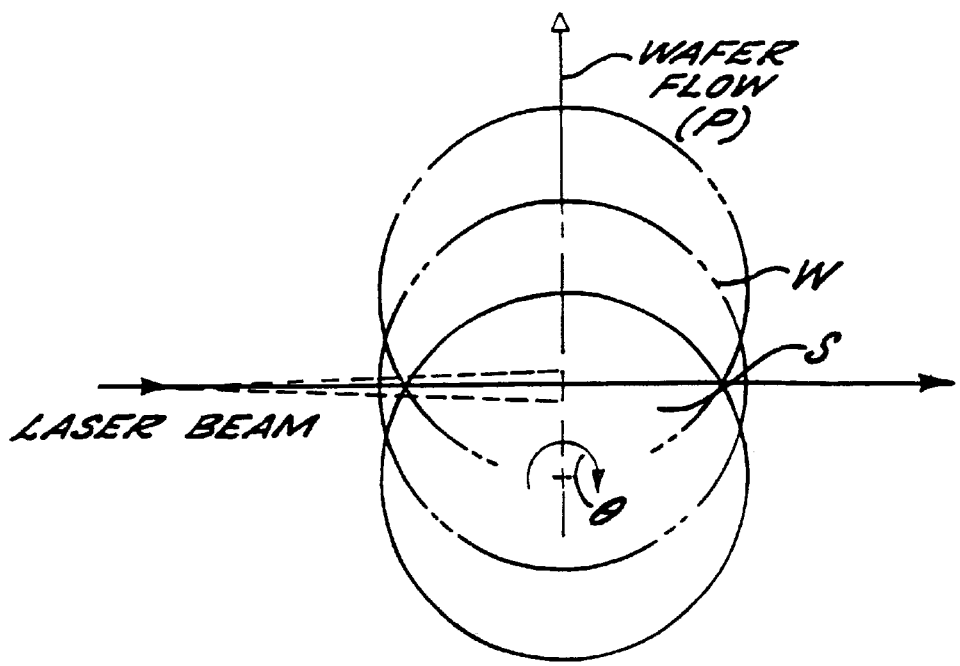
FIG. 5 schematically illustrates rotational and translational travel of a wafer through an inspection area according to the present invention.

As best illustrated in FIGS. 1–3, the surface inspection system 20 preferably includes means for translationally transporting a workpiece W along a material path P. The means for transporting a workpiece W is illustrated as a transporter 40 arranged to translationally transport a workpiece W along a material path P and preferably through an inspection zone or area Z. The translational transporter 40, as illustrated, preferably includes a gear 42, a motor 41 including a shaft 41a arranged for rotating the gear 42, and guides 36, 37 having teeth formed integral therewith. The motor 41 and gear 42 mounted on the motor shaft 41a form a chuck for the system 50. The motor 41 of the chuck is preferably mounted to a stage member 43 having a plurality of flanges 43a extending upwardly therefrom which receives the workpiece W, i.e., silicon wafer, thereon along edges of the workpiece W as illustrated. This mounting technique for the workpiece W reduces smudges or other surface problems which may be associated with positioning the lower surface of the workpiece so as to abuttingly contact an upper surface of the stage member 43. The stage member 43 preferably is translationally transported along stage guide members 38, 39 secured to an underside thereof. Other translational and/or rotating means such as a piston and cylinder configuration mounted to the stage member and a motor for rotating the stage member as understood by those skilled in the art may also be used according to the invention.

Also, means for rotating a workpiece W, illustrated as a rotator 45, is associated with the transporter 40 and arranged to rotate a workpiece W during translational travel along the material path P. The rotator 45 as illustrated preferably includes a motor 46 mounted to an underside of the stage member for providing rotation of the wafer mounted thereon at a predetermined speed. The transporter 40 and the rotator 45 preferably are synchronized and arranged with a scanner 80 so as to form a spiral-shaped narrow angle scan (a) across the surfaces of the workpiece during rotational and translational travel along the material path P.

As illustrated in FIGS. 1 and 3–5, a scanner 80 is positioned and arranged to scan a surfaces of a workpiece w during rotational and translational travel along the material path P. It will also be understood, however, by those skilled in the art that the scanner 80 may be arranged for rotational and/or translational movement while the workpiece W is stationary, or translationally or rotatively moved. In addition, other material paths P may be used, e.g., neither the workpiece W nor the scanner 80 may be translationally moved and the workpiece tested in only a rotational path. Accordingly, the present invention includes a P-polarized light source 81 or a light source coupled with a P-polarized filter positionally aligned with the light source to generate a P-polarized light beam B therefrom, means for receiving the light source and scanning a surface S of a workpiece W, i.e., a mirror 82, lenses 84, 86, deflector 85, and means for imparting a rotational and translational scan of the workpiece W, i.e., the transporter 40 and the rotator 45.

The scanner 80 preferably includes a light source 81, i.e., laser, arranged to either generate a P-polarized light beam B therefrom or coupled with a P-polarized filter positionally aligned with the light source. The P-polarized light preferably has a spot size which includes a full width, halfmaximum of less than 0.1 millimeters. The scanner also includes means positioned to receive the light beam B and arranged for scanning the light beam B along a relatively narrow scan path (a) across a surface S of the workpiece W as the workpiece W rotationally and translationally travels along the material path P. The light source 81 is preferably a visible-light laser with a relatively short wavelength, such as Argon-Ion or solid state, as understood by those skilled in the art. The laser 81 is also preferably the combination of a laser with external optics as understood by those skilled in the art. The laser 81 preferably has a beam diameter of about 0.6 millimeters ("mm").

The scanning means preferably includes a deflector 85, as illustrated, positioned to receive the light beam B and arranged to deflect the light beam B along a relatively narrow scan path ($\alpha$). The deflector 85 is preferably an acousto-optical (AO) deflector as illustrated (or a mechanical deflector), and the relatively narrow scan path ($\alpha$) is preferably no greater than 0.1 radians and, more particularly, in the range of 0.025–0.040 radians. The scan path $\alpha$ preferably directionally corresponds to the path P of translational travel and, as best illustrated in FIG. 4, preferably is in a generally parallel direction therewith as illustrated by the arrows. The deflection is accomplished by exciting a crystal with high frequency sound waves, for example, which interact with the incident light wave in such a way to shift the light beam B and thereby change the angle of propagation. It will be understood that various frequencies of the crystal will responsively cause the light passing therethrough to be deflected at correspondingly various angles of propagation. If the frequency of the sound waves is swept in a sawtooth pattern, the laser beam B is scanned through an angle ($\alpha$) proportional to the frequency. The AO deflector 85 preferably provides a constant scanning speed which, in turn, provides a consistent or a predetermined time response for particles or defects detected from an article surface. Although the present invention is described with reference to an AO deflector 85, other means for providing narrow angle scans as understood by those skilled in the art, such as a galvanometer, a piezoelectric scanner, a resonant scanner, a rotating mirror, a scanning head, other electronic scanners, or the like, may also be used according to the present invention.

Also, a beam expander 82 is preferably positioned between the laser source 81 and the deflector 85 to expand the light beam B prior to entering the acousto-optical deflector 85. The beam expander 82 preferably provides means for more fully filling the active aperture of the deflector 85 to best utilize the scan angle of the deflector 85.

The scanner 80 also preferably includes means positionally aligned with the deflector 85 and arranged for directing the light beam from the narrow scan path ($\alpha$) toward a surface S of a workpiece W at a relatively low angle of incidence ($\theta_i$) (relative to the workpiece surface) as the workpiece W rotatively and translationally travels along the material path P. Although a low angle of incidence ($\theta_i$) is preferred, the angle of incidence ($\theta_i$) may be any angle other than normal to the workpiece W to provide the advantages of the present invention. The angle of incidence is preferably greater than 45 degrees from normal to the article surface, i.e., less than 45 degrees from the surface of the workpiece W and, more particularly, is preferably in the range of 65–85 degrees from normal to the article surface.

The directing means is illustrated as a mirror 82 and a plurality of optical lenses 84, 86 arranged to direct the light beam B from the laser 81 toward the surface S of the workpiece W to be inspected. As the light beam B travels from the AO deflector 85, the beam B passes through a cylindrical lens 84 which preferably angularly orients the light beam B for a linear scan of the surface of the article during translational and rotational movement of the article through the inspection zone. A stop member 87 is positionally aligned with the cylindrical lens 84 positioned closely adjacent the AO deflector 85 to stop the relatively small portion of light which is not linearly oriented for the scan of the surface of the workpiece W. The optical lens 86 positioned after the cylindrical lens 84 is a focusing or f-theta lens, as understood by those skilled in the art, arranged for focusing the light beam on the surface of the workpiece W.

The scanner 80 according to the present invention preferably scans the beam of light B in a radial direction with rotating motion and linear, lateral, or translational motion (Y) to implement a spiral scan pattern as best illustrated in FIG. 3. Nevertheless, any other material path P for the workpiece W may also be used to provide the advantages of the invention.

As best illustrated in FIGS. 1, 3, 3A, and 6–7, means for collecting light from the surface of a workpiece is preferably a collector 100 having a light channel detector 110 arranged for detecting light specularly reflected from the surface S of a workpiece W and a dark channel detector 120 positioned adjacent the light channel detector 110 for detecting light scattered from the surface S of a workpiece W. The light channel detector 110 may be a PMT or a photodiode, but preferably, as understood by those skilled in the art, is a quadrant-cell device, i.e., detector, arranged for X-Y coordinate positioning detection so that deviation in the path of reflected light, i.e., during detection of a defect or particle, may be determined. Such quadrant-cell detectors are manufactured by Advanced Photonix, Inc., formerly Silicon Detector Corp., of Camarillo, Calif. Although a particular configuration is illustrated, it will be understood that various other rectangular or multiple cell, i.e., bi-cell, configurations may also be used according to the present invention.

The dark channel detector 120 preferably includes a plurality of collectors 121, 123, 125 positioned closely adjacent each other and arranged for collecting components of the scattered light at different respective predetermined angles from the surface S of the workpiece W. The plurality of collectors 121, 123, 125 of the dark channel detector 120 form segmented optics having at least two collectors positioned adjacent each other. The plurality of collectors 121, 123, 125 as illustrated will be understood by those skilled in the art to be compound lenses, and other lens arrangements may also be used according to the present invention. The plurality of collectors 121, 123, 125 respectively include a forward channel collector 121 arranged to collect light components scattered forwardly from the surface S of the workpiece W at a relatively small angle a, a center channel collector 123 positioned closely adjacent the forward channel collector 121 and arranged to collect light components scattered substantially normal from the surface S of the workpiece W at a relatively medium angle b, and a back channel collector 125 positioned closely adjacent the center channel collector 123 and arranged to collect light components scattered backwardly from the surface S of the workpiece W at a relatively large angle c. The dark channel detector 120 further includes a forward channel detector 122, a center channel detector 124, and a back channel detector 126 each respectively positioned in optical communication with a corresponding collector 121, 123, 125, and means electrically connected to the forward, center and back channel detectors 122, 124, 126 and responsive to electrical signals from said detectors for determining the presence of a particle on the surface S of a workpiece W. The determining means of the collector is preferably electronic signal discrimination circuitry 150, such as illustrated (see FIGS. 3 and 7) and understood by those skilled in the art, which receives signals representative of collected light from the light channel detector 110 and the dark channel detector 120.

Figure 6:
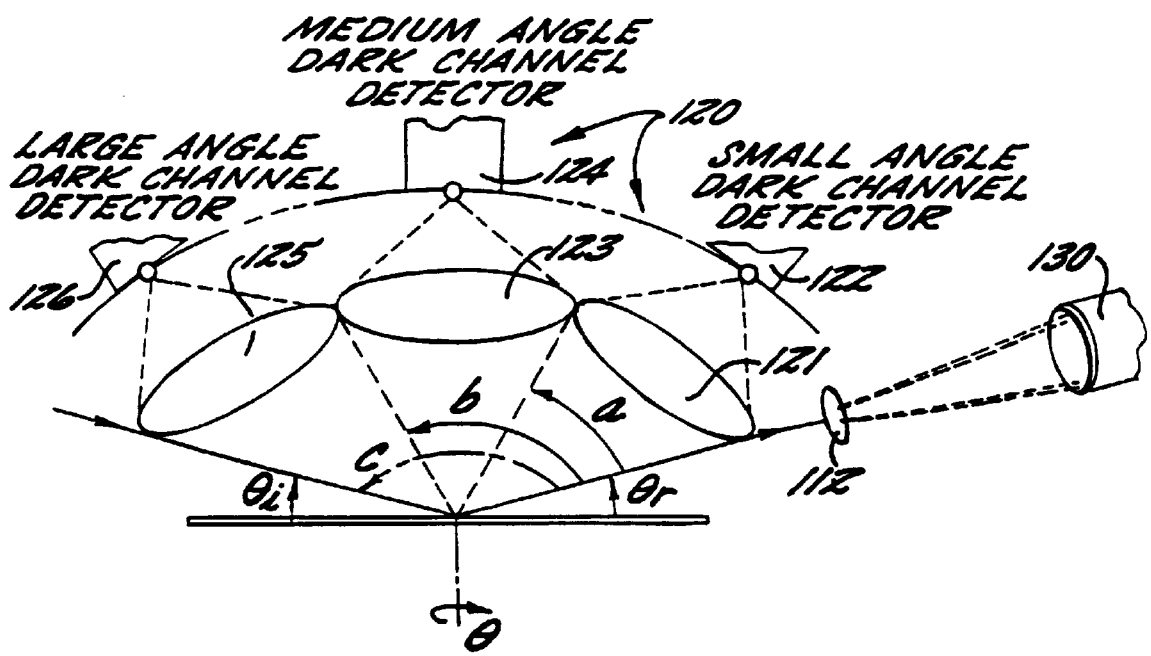
FIG. 6 schematically illustrates a collector of a surface inspection system having segmented optics for collecting light scattered from a surface of a wafer according to the present invention.

As best illustrated in FIGS. 1, 3, and 6, the relative respective angles a, b, c of the plurality of collectors 121, 123, 125 are preferably determined with respect to the angle of reflection ($\theta_r$) of light from the surface S of the workpiece W and with respect to forward a, backward c, and substantially normal b light component scattering which occurs relative to the angle of incidence $\theta_i$ of the scan. For example, if the angle of incidence $\theta_i$ is relatively low with respect to the surface plane (high with respect to normal), e.g., 15° from horizontal or −75° from normal, then the forward scattering or small angle a is preferably about +22° to +67°, the substantially normal scattering or medium angle is about −25° to +20°, and the backward scattering or large angle is about −72° to −27°. In addition, the advantages of the present invention have been realized, for example, where the angle of incidence $\theta_i$ is 25° from horizontal or −65° from normal with P-polarized visible light having a wavelength of 488 nm, the back channel collector is centered at −38°, and the center channel collector is centered at +10°. When a particle or defect is detected, for example, the forward channel collector 121 is positioned to receive and collect forward scattering a, the center channel collector 123 is positioned to receive and collect substantially normal scattering b, and the back channel collector 125 is positioned to receive and collect back scattering c from the surface of the workpiece with respect to the detected particle or defect, or the like. In the direction generally perpendicular to the plane of incidence, approximately 73° of total angle is captured in the above example. This is about 0.64 steridians of solid angle per segment or a total of about 1.92 steridians which is a substantial improvement over previous known detectors.

Figure 7:
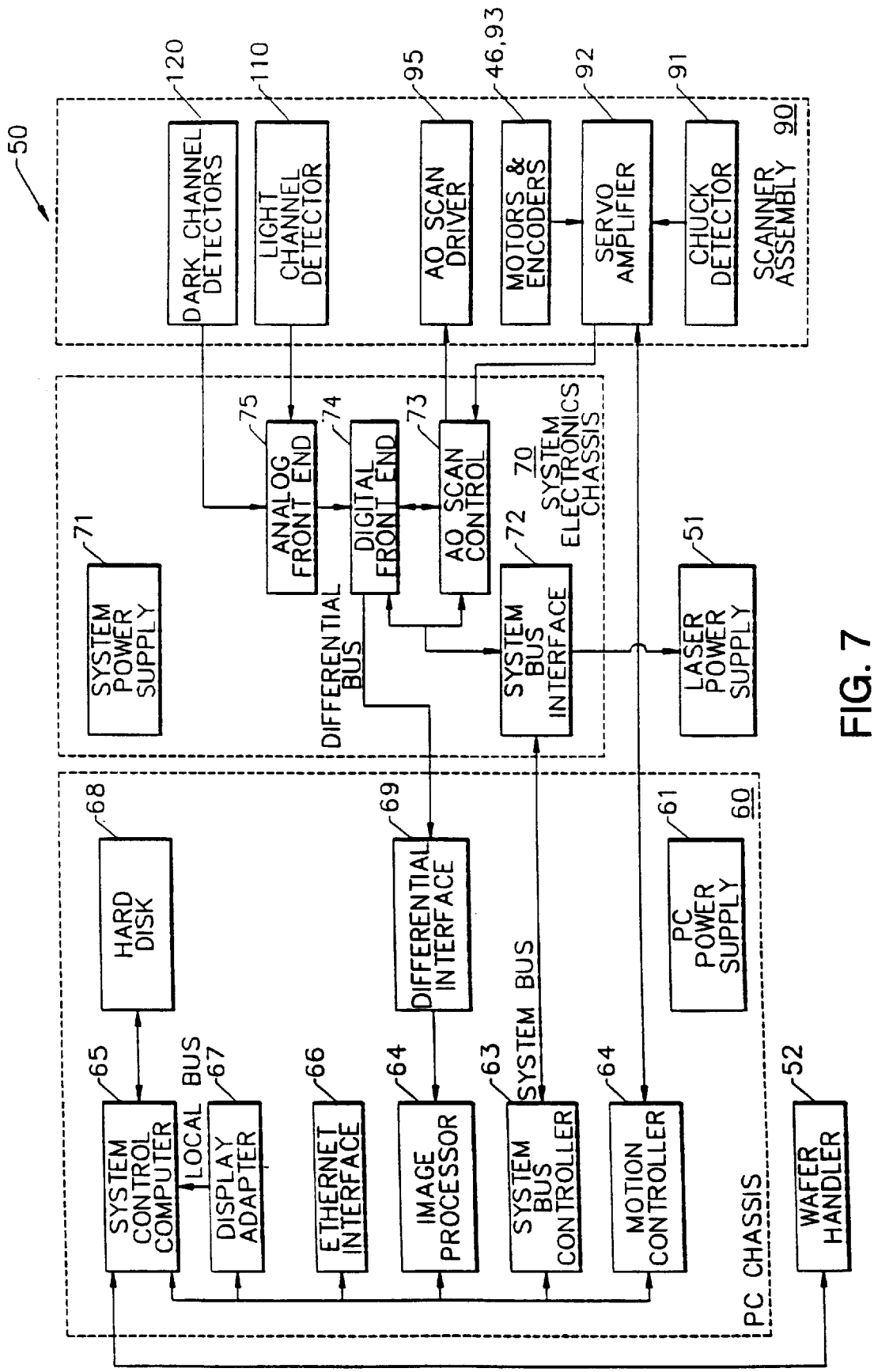
FIG. 7 schematically illustrates a system controller of a surface inspection system according to the present invention.
Figure 8B:
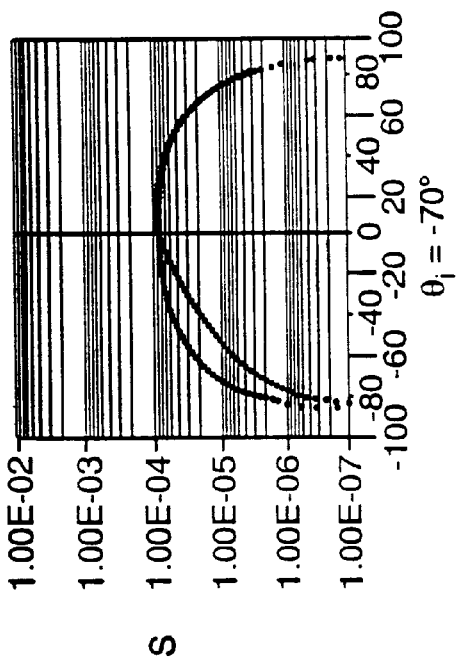
FIG. 8a–d illustrates a comparison between using S-polarized and P-polarized light at normal and non-normal angles of incidence to distinguish pits and particles in and on the surface of a wafer.
Figure 8D:
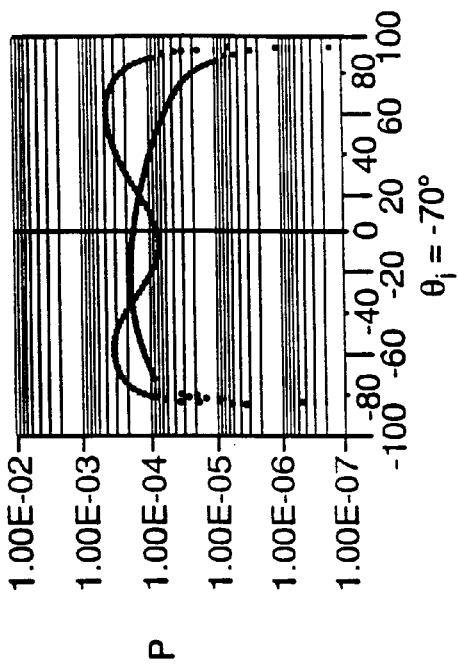
Figure 8A:
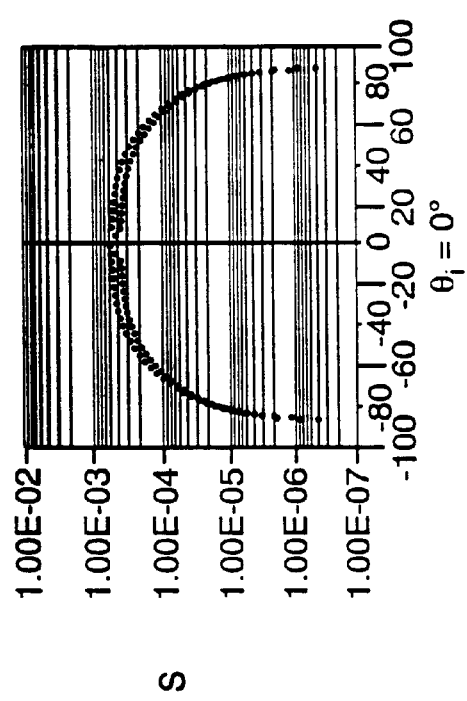
Figure 8C:
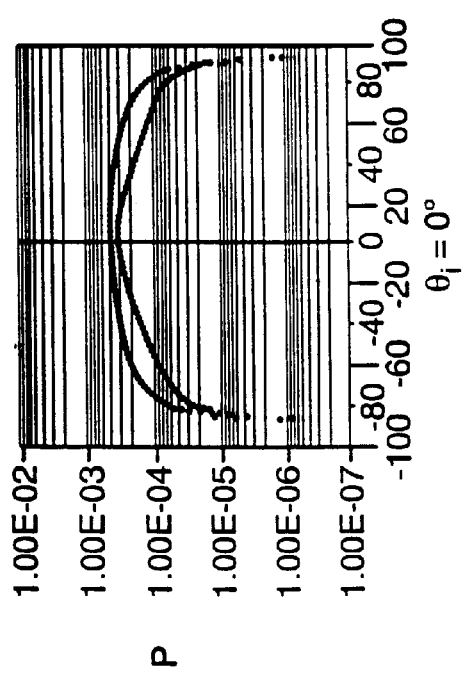

As best illustrated in the perspective view of FIG. 1 and the schematic view of FIG. 7, the surface inspection system 20 preferably is computer controlled. The system controller 50 operates the inspection system 20 under the supervision and direction of a human operator, stores and retrieves data generated by the system 20, and performs data analysis preferably responsive to predetermined commands. The scanner assembly portion 90 illustrated cooperates with the scanner 80 and includes a chuck detector 91 which transmits a position to a servo-amplifier 91. The relative position of the article being inspected is communicated to the system 50 via motors 41, 46 and encoders 93 mounted thereto. The position data is transmitted to the AO scan control 73 which preferably forms a portion of the system electronics chassis 70 and which responsively drives the AO deflector 85 via a AO scan driver 95.

The system electronics chassis 70 includes a system power supply 71 and receives signals from the dark channel detectors 120 and the light channel detector 110 respectively representative of the scattered and the specularly reflected light. As understood by those skilled in the art, these data signals are conventionally electrically communicated in an analog format to analog front end electronics 75 and are converted to digital format by digital front end electronics 74 or the like. The digital front end electronics 74 also cooperates with the AO scan control 73, the system bus interface 72, and the differential interface 69, i.e., differential bus, of the personal computer ("PC") chassis 60. The system bus interface 72 also communicates with a laser power supply 51 of the surface inspection system 50.

The PC chassis 60 includes a PC power supply 61 arranged for supplying power to the PC. The PC chassis 60 also has a motion controller 64 which responsively communicates with the servo amplifier 92 of the scanner assembly 90 and a system control computer 65, i.e., microprocessor, or controller. The system control computer 65 preferably electrically communicates with a wafer handler 52 for responsively sending and receiving predetermined command signals for mounting and handling the article or wafer being inspected as set forth above. The system control computer 65 also preferably communicates with a hard disk drive 68, a display adapter 67 arranged to communicate with the display, and an ethernet interface 66 arranged for network or other system 50 communication. An image processor 64 electrically communicates with the differential interface 69 and the system control computer 65 for processing the image of the surface of the inspected article and/or defects, flaws, undulations, or particles thereon. The surface inspection system 50 as illustrated in FIG. 7, and as understood by those skilled in the art, preferably is formed of a combination of software and hardware which forms these various components, or combinations thereof, of the system 50.

As illustrated in FIGS. 1–7, methods of inspecting a surface S of an article or workpiece W for defects are also provided according to the present invention. A method of inspecting a surface S of a workpiece w preferably includes rotatively and translationally transporting a workpiece W along a material path P and scanning a relatively narrow scan path α of light across a surface of the workpiece W as the workpiece W travels along the material path P. The step of rotatively and translationally transporting a workpiece along a material path preferably is synchronized with the step of scanning a surface of the workpiece so as to impart a substantially spiral-shaped scan of the surface of the workpiece. Light specularly reflected from and light scattered from the surface S of the workpiece W preferably are separately collected. The light which is scattered from the workpiece surface is collected as separate light components at different angles. For example, light components scattered substantially normal from the surface S of the workpiece W and light components scattered backwardly from the surface S of the workpiece W are separately collected and compared to thereby ascertain differences in the angular distribution of the scattered light. Light scattered from the surface S of the workpiece W is separately collected by a plurality of collectors 121, 123, 125 at a plurality of predetermined scattering angles a, b, c. Preferably, the collectors are positioned to collect forwardly scattered light components, backwardly scattered light components, and light components scattered in a direction substantially perpendicular to the surface of the workpiece. Light detected by the various collectors signifies a defect in or on the surface S of the workpiece W.

In order to determine whether the defect is a particle defect or a pit, differences in the angular distribution of the light scattered from the workpiece are detected. This is achieved by comparing the amount of light collected by one of the collectors to the amount of light collected by one or more of the other collectors. The light detected by the detectors 122, 124 and 126, particularly the center channel detector 124 and the back channel detector 126 can be used to distinguish particles located on the workpiece surface from pits located in the workpiece surface when P-polarized light is used in the scanner. Specifically, when the defect is a pit in the workpiece surface, P-polarized light scattered from the workpiece surface forms a pattern in which the amount of light scattered to the center channel collector 124 is greater than the amount of light scattered to the back channel collector 126. This has been found to be particularly the case with small pits, i.e., pits having a diameter of no more than about 300 nm. In contrast, when the defect is a particle on the workpiece surface, P-polarized light scattered from the wafer surface forms a pattern in which the amount of light scattered to the center channel collector 124 is less than the light scattered to the back channel collector 126. FIGS. 8–15 show examples of the scattered light distributions for pits and particles of various sizes when P-polarized light is used. FIG. 8 is a comparison between scatter diagrams for 90 nm tungsten particles on the surface of the workpiece and 180 nm pits in the surface of the workpiece.

As seen from the two scatter diagrams on the left side of FIG. 8, the use of either S-polarized light and the use of a normal or perpendicular angle of incidence, i.e., $\theta_i=0°$, with either S or P-polarized light does not provide an effective method of distinguishing the particles from the pits in the surface of the workpiece. The angular distribution of the light scattered from the workpiece is substantially similar for pit defects and for particle defects. Likewise, as seen from the scatter diagram in the upper right quadrant, when S-polarized light is used at a non-normal angle of incidence, for example $\theta_i=-70°$, there is relatively little difference in the shape of the scatter curves for pits and for particles. However, when P-polarized light is used, as seen from the diagram in the lower right quadrant, the particles scatter light in such a way that a dip is detected in the region approximately perpendicular to the workpiece surface. The pits create a distinctly different angular distribution pattern, by which pits can be distinguished from particles.

Figure 9:
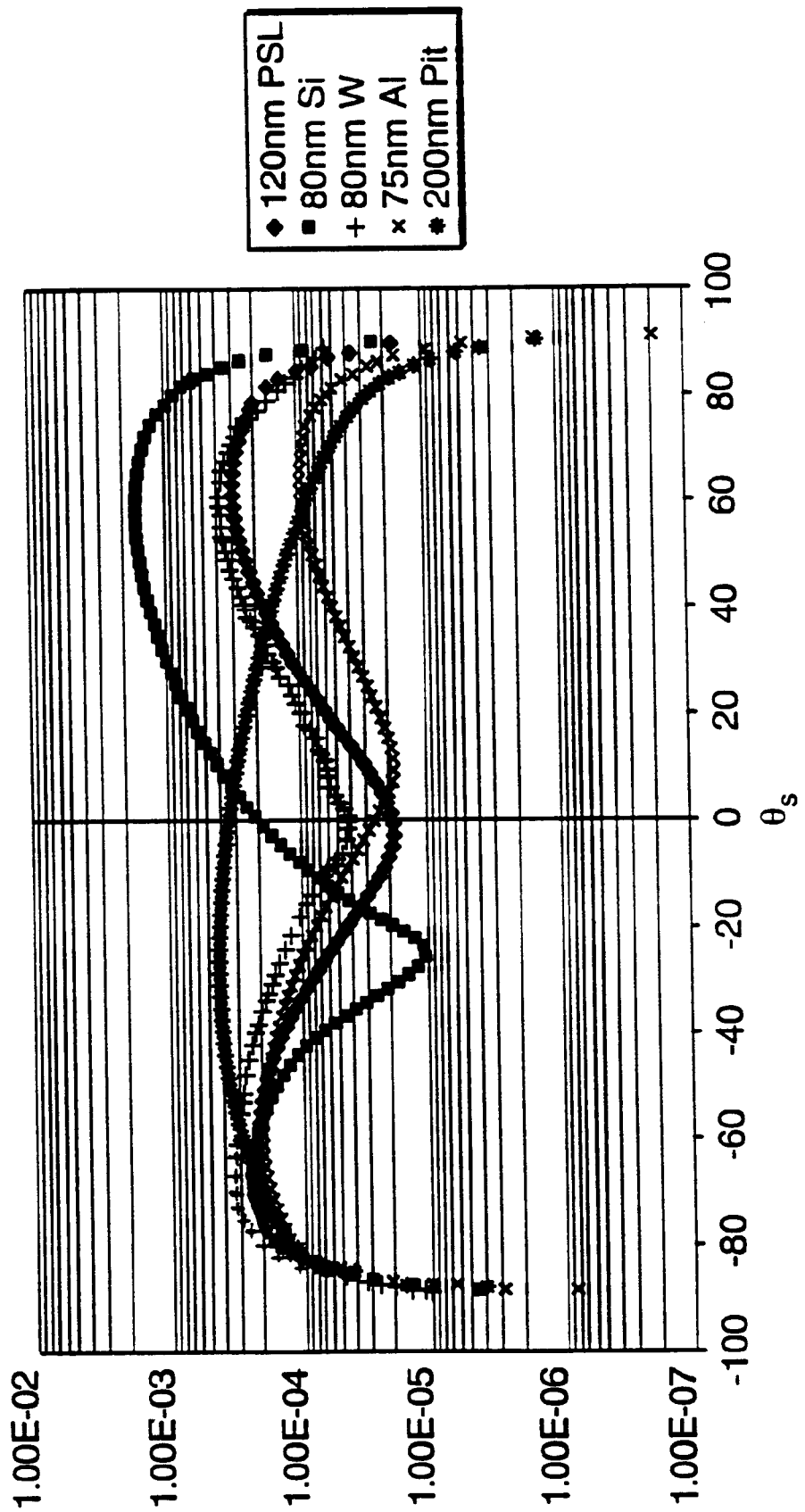
FIG. 9 illustrates the use of P-polarized light at a non-normal angle of incidence in detecting pits and several types of particles in and on the surface of a wafer.

FIG. 9 illustrates the angular distribution patterns obtained from various particle materials. When P-polarized light is used at an angle of incidence, $\theta_i=-70°$, the particles may be distinguished by a characteristic dip in the region approximate the angle normal the workpiece surface (0°) thus allowing the presence of particles on the surface of the workpiece to be distinguished from the presence of pits within the workpiece. Specifically, the 120 nm psl particles, the 90 nm silicon particles, the 80 nm tungsten particles, and the 75 nm aluminum particles all exhibit a characteristic dip in the vicinity of the direction normal or perpendicular to the surface of the workpiece (0°). The specific minimum point varies for each particle, but all are generally within a region covering ± about 25° from the 0 or perpendicular direction. The scattering pattern from the pit does not exhibit a dip.

Figure 10B:
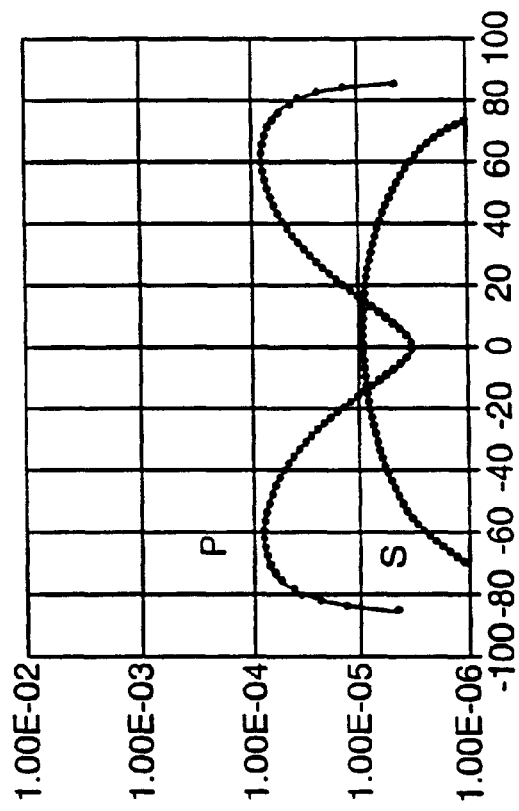
FIG. 10a–b illustrates a comparison between using P-polarized and S-polarized light in detecting a particle on the surface of a wafer and provides both experimental and modeled results.
Figure 10A:
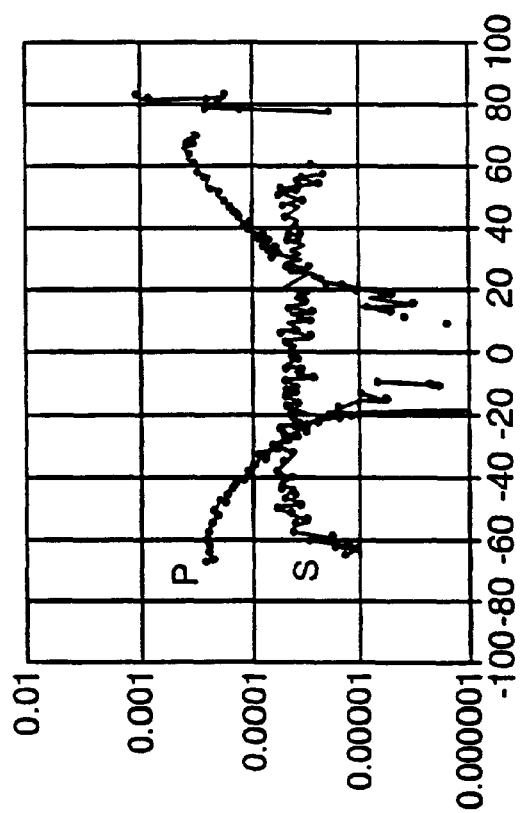

FIG. 10 compares the angular distributions for modeled results and experimental results using a 0.1 micron psl sphere with a laser beam at a wavelength of 488 nm and a −75° angle of incidence using both P-polarized light and S-polarized light. As shown, the P-polarized light produces a characteristic dip in the vicinity of 0°. No such dip occurs using S-polarized light.

Figure 11:
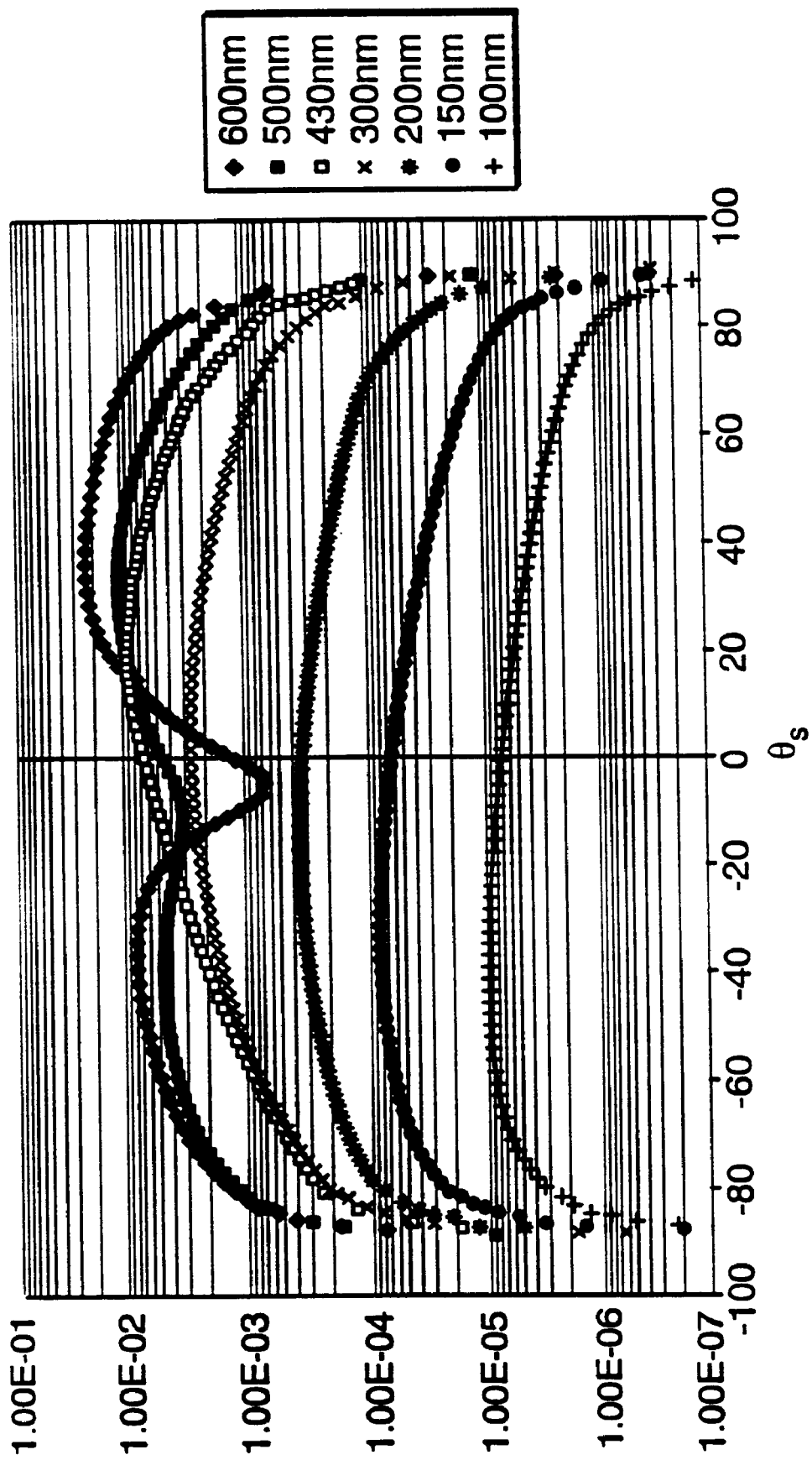
FIG. 11 illustrates the use of P-polarized light at a non-normal angle of incidence in detecting scattered light for pits of various diameters in the surface of a wafer.

FIG. 11 illustrates modeled scatter for pits of various diameters. As shown in FIG. 11, when P-polarized light is used at an angle of incidence, $\theta_i=-70°$, the amount of backwardly scattered light is greater than the amount of forwardly scattered light for small pits. This is particularly the case where the diameter of the pit is no more than about 300 nm.

Figure 12:
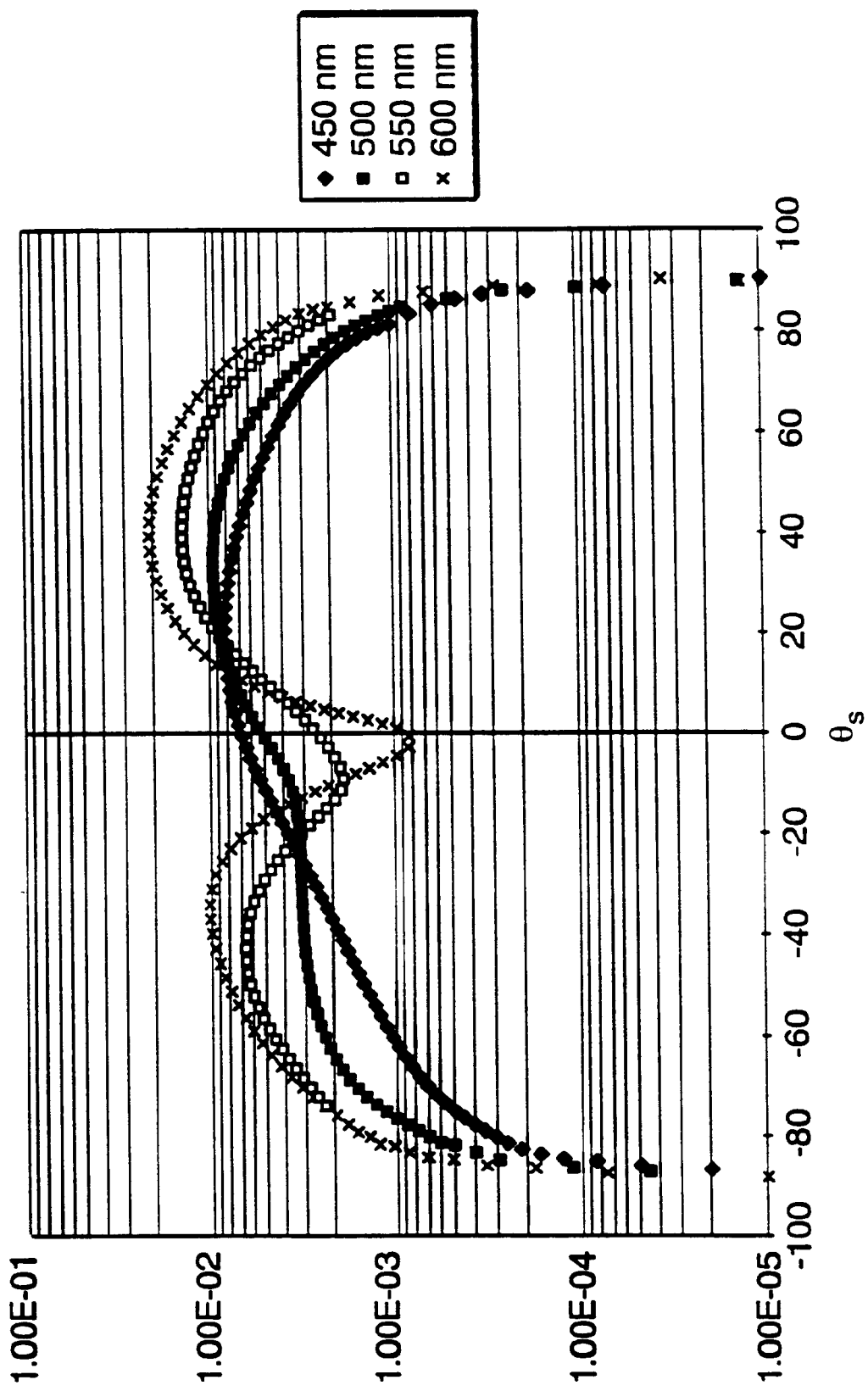
FIG. 12 illustrates the use of P-polarized light in detecting pits of various diameters in a wafer.

FIG. 12 illustrates the angular distribution of light scattered by larger pits, i.e., pits having a diameter of more than about 430 nm, located in the surface of the workpiece.

Figure 13:
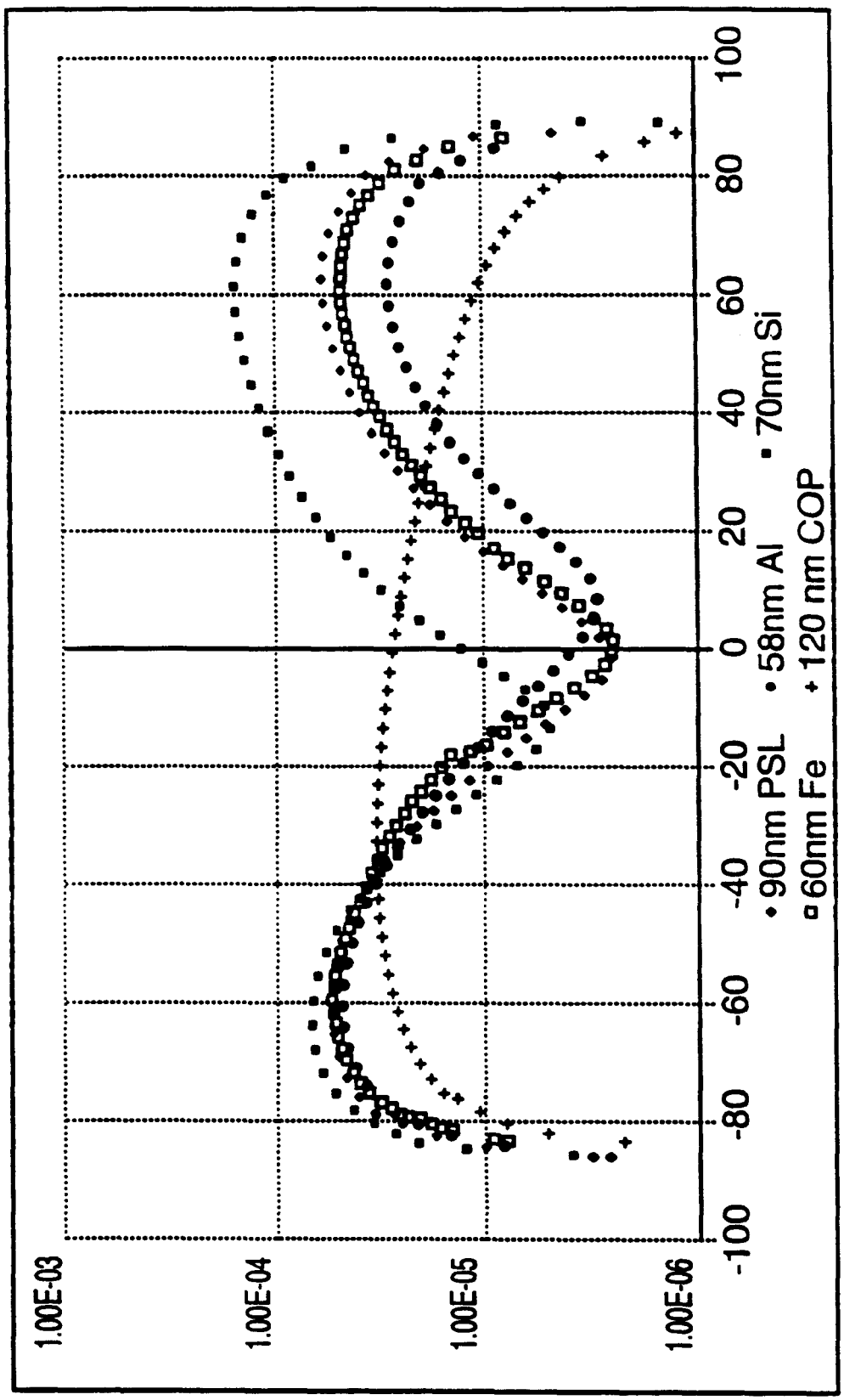
FIG. 13 illustrates the angular distribution pattern of relative small COPS and particles using P-polarized light at a non-normal angle of incidence.
Figure 14:
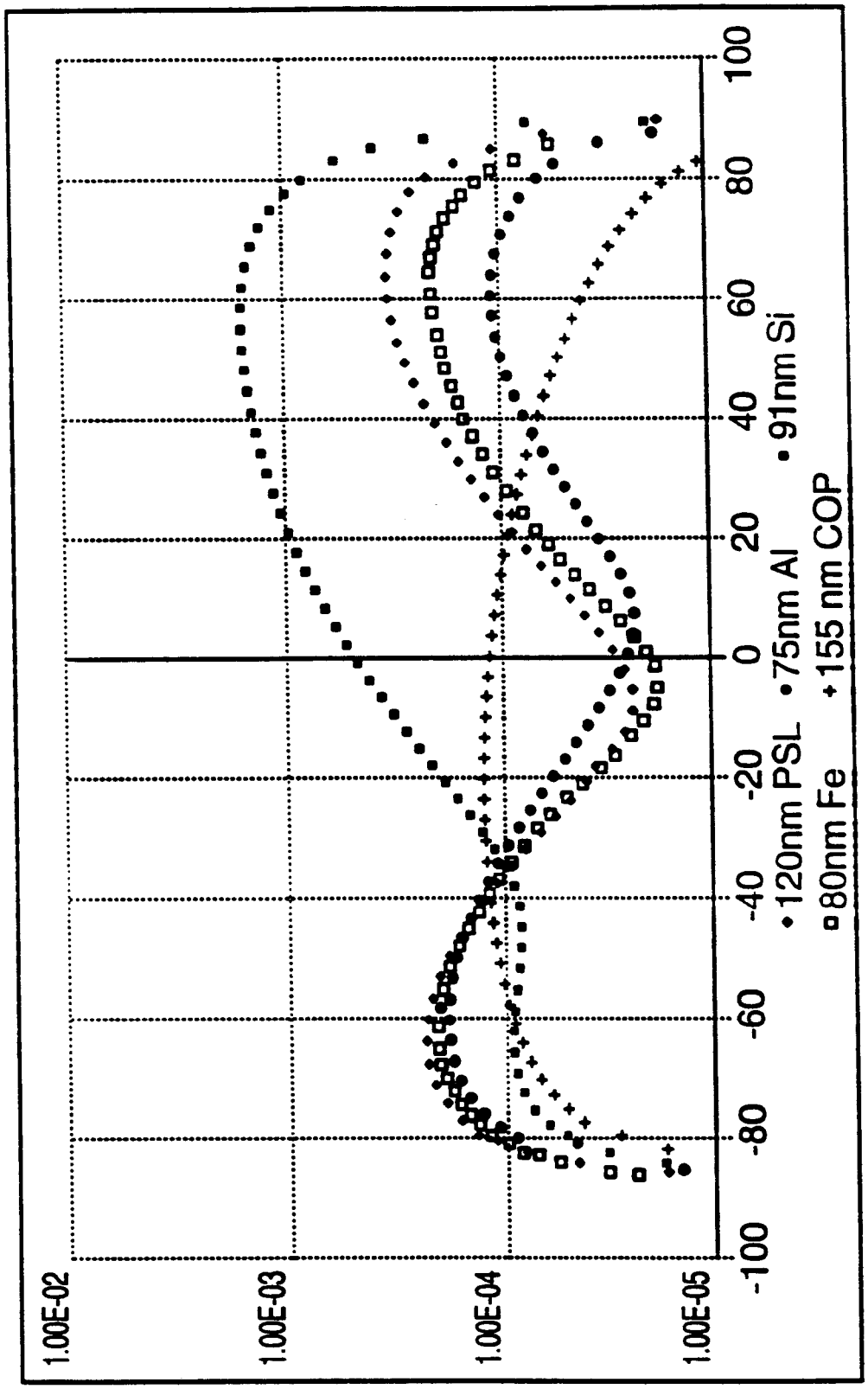
FIG. 14 is an illustration similar to FIG. 13 showing the angular distribution pattern of medium size COPS and particles.
Figure 15:
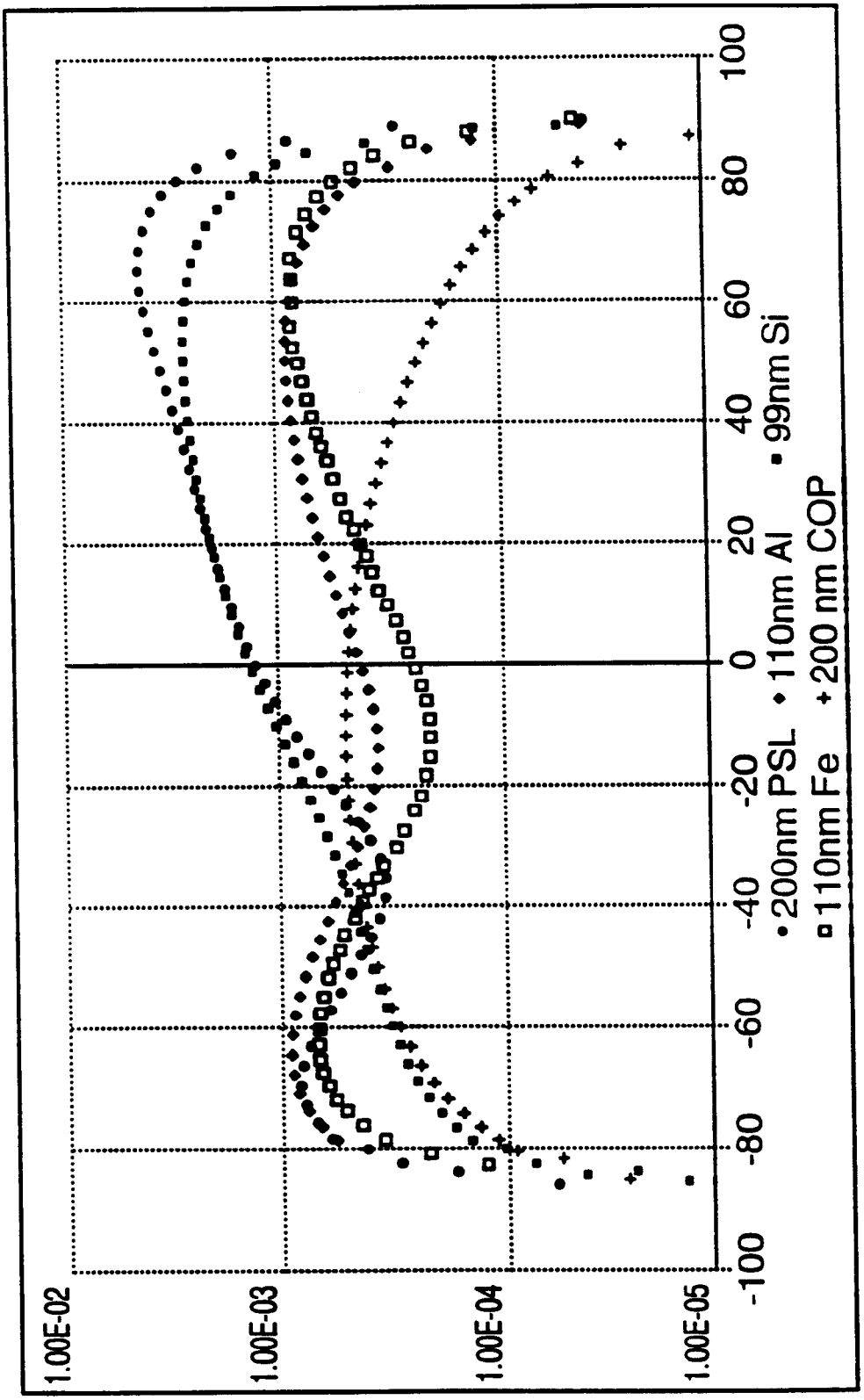
FIG. 15 is an illustration similar to FIG. 13 showing the angular distribution pattern of larger size COPS and particles.

FIGS. 13, 14 and 15 illustrate representative angular distribution patterns for small COPS, medium COPS and large COPS respectively, versus particles using P-polarized light at an angle of incidence of −70°. In FIG. 13, it will be seen that a 120 nm cup exhibits a convex shaped distribution pattern, with the amount of light backscattered at angles ranging from −20 to −60 being higher than the light forwardly scattered at angles of +20 and above. Particles of various compositions with sizes of 90 nm and below all exhibit a characteristic concave distribution pattern, with a "dip" in the vicinity of 0°. For the larger sized particles, e.g. 90 mn psl, the intensity of forwardly scattered light is greater than the backscattered light.

As seen from FIG. 14, the angular distribution pattern for a somewhat larger 155 nm COP is generally similar to the 120 nm cup of FIG. 13, with the amount of backscattered light at angles of from −20 to −80 being greater than the amount of forwardly scattered light. The smaller sized particles, e.g. 91 nm and smaller consistently exhibit a concave distribution pattern with a "dip" at or near 0°, and with the amount of forwardly scattered light being greater than the amount of backscattered light. The larger particles (120 nm psl) show a markedly greater difference between the amount of forwardly scattered light and backscattered light. This trend is also seen in FIG. 15 with particles as large as 200 nm.

Figure 16:
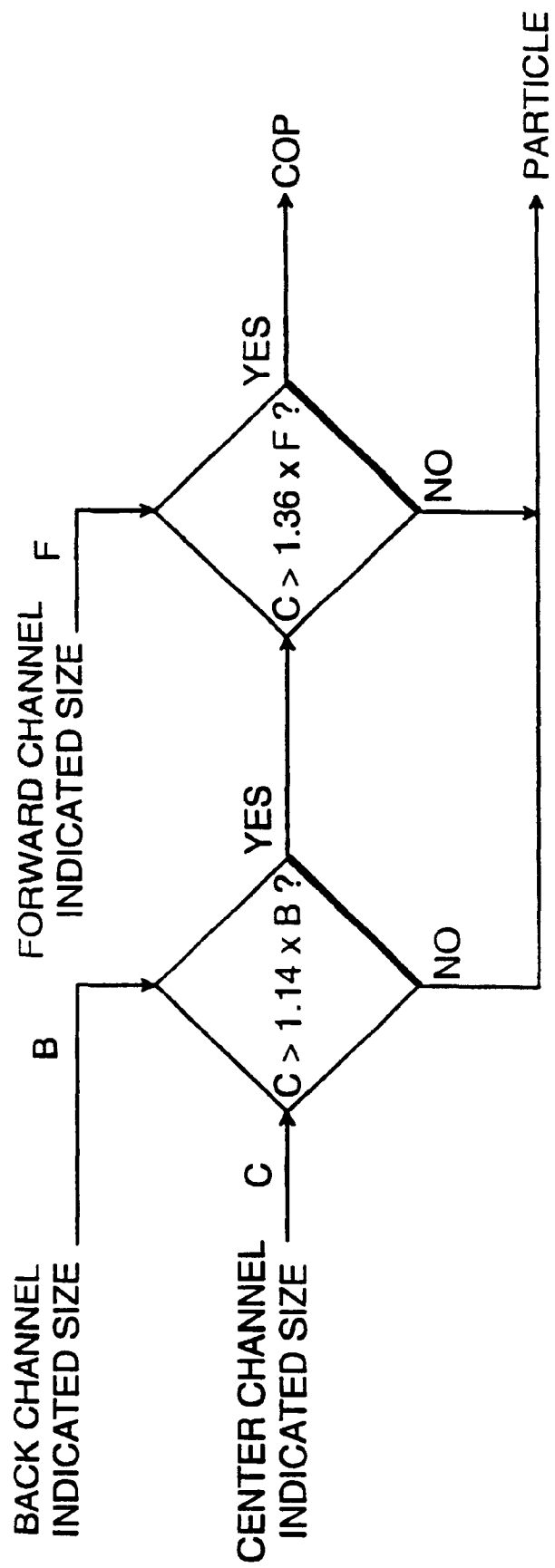
FIG. 16 is a flowchart illustrating the application of an algorithm for distinguishing between COPS and particles.

From these characteristic angular distribution patterns, it is possible to distinguish COPS from particles. In particular, if the ratio of the intensity of the signal from the center channel detector 124 to the signal from the back channel detector 125 is less than a predetermined amount, the defect may be classified as a particle. If the ratio of the intensity of the center channel detector 124 signal to the forward channel 122 detector signal is more than a predetermined amount, the defect may be classified as a pit. FIG. 16 illustrates one suitable algorithm for analyzing the information from the detectors to distinguish particles from COPS. If the ratio of the center channel indicated size C to the back channel indicated size B is less than the predetermined constant, in this instance 1.14, then the defect is classified as a particle. Stated otherwise, a signal event B representing the back channel indicated size and a signal event C representing the center channel indicated size are directed to a comparator where the value of C is compared to the value of B times a predetermined constant, in this instance 1.14. If C is not greater than 1.14 times B, then the signal event is classified as a particle. If C is greater than 1.14 times B, then C is compared to a value F representing the forward channel indicated size. If C is greater than a predetermined constant (in this instance 1.36) times the value of F, then the signal event is classified as a COP. If not, the event is classified as a particle.

Figure 17:
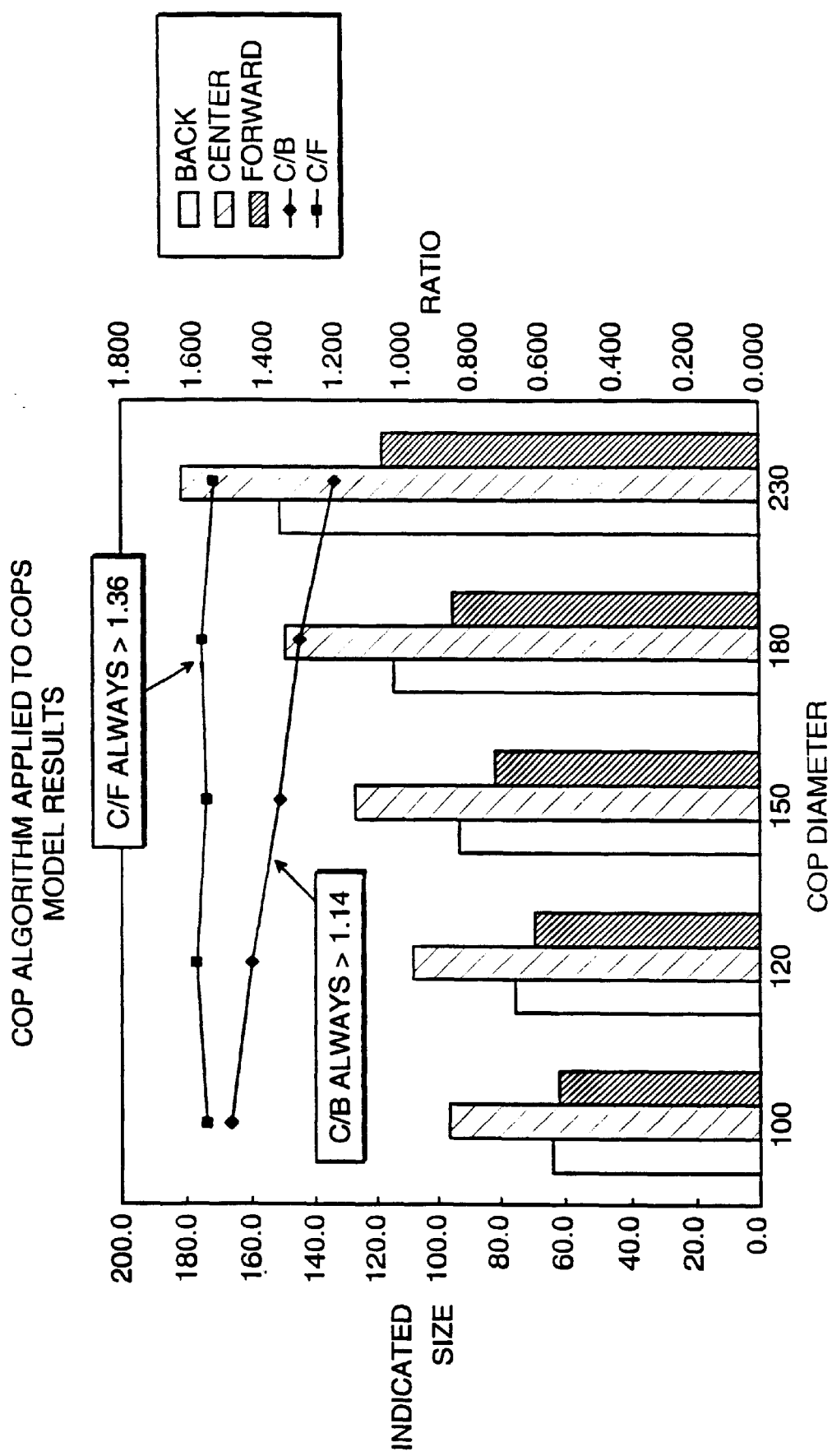
FIGS. 17 and 18 are graphs illustrating how the constants for the algorithm of FIG. 16 may be derived.
Figure 18:
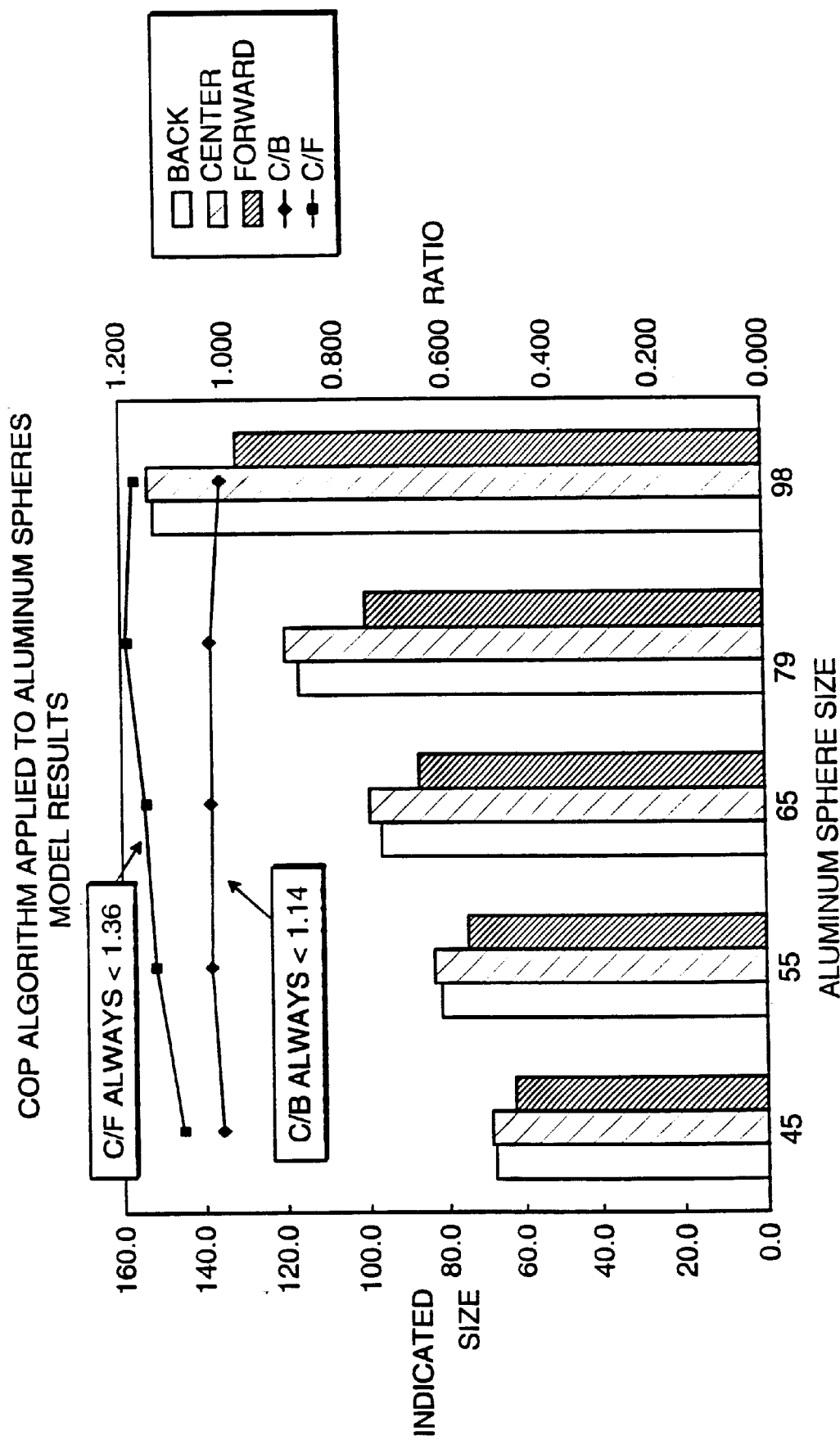

The application of this algorithm as applied to COPS is graphically illustrated in FIG. 17. The application of this algorithm to particles, in this instance aluminum particles, is graphically illustrated in FIG. 18. FIGS. 17 and 18 illustrate how modeled data or experimental data for particles or COPS of various sizes can be used to derive constants for use in the type of algorithm shown in FIG. 16. It should be apparent to those of skill in the art from this illustration that the present invention is not limited to the particular algorithm described herein, and that other approaches and other specific algorithms may be used to process the data obtained from the various detectors and to distinguish between pits and particles in accordance with the present invention.

Figure 19:
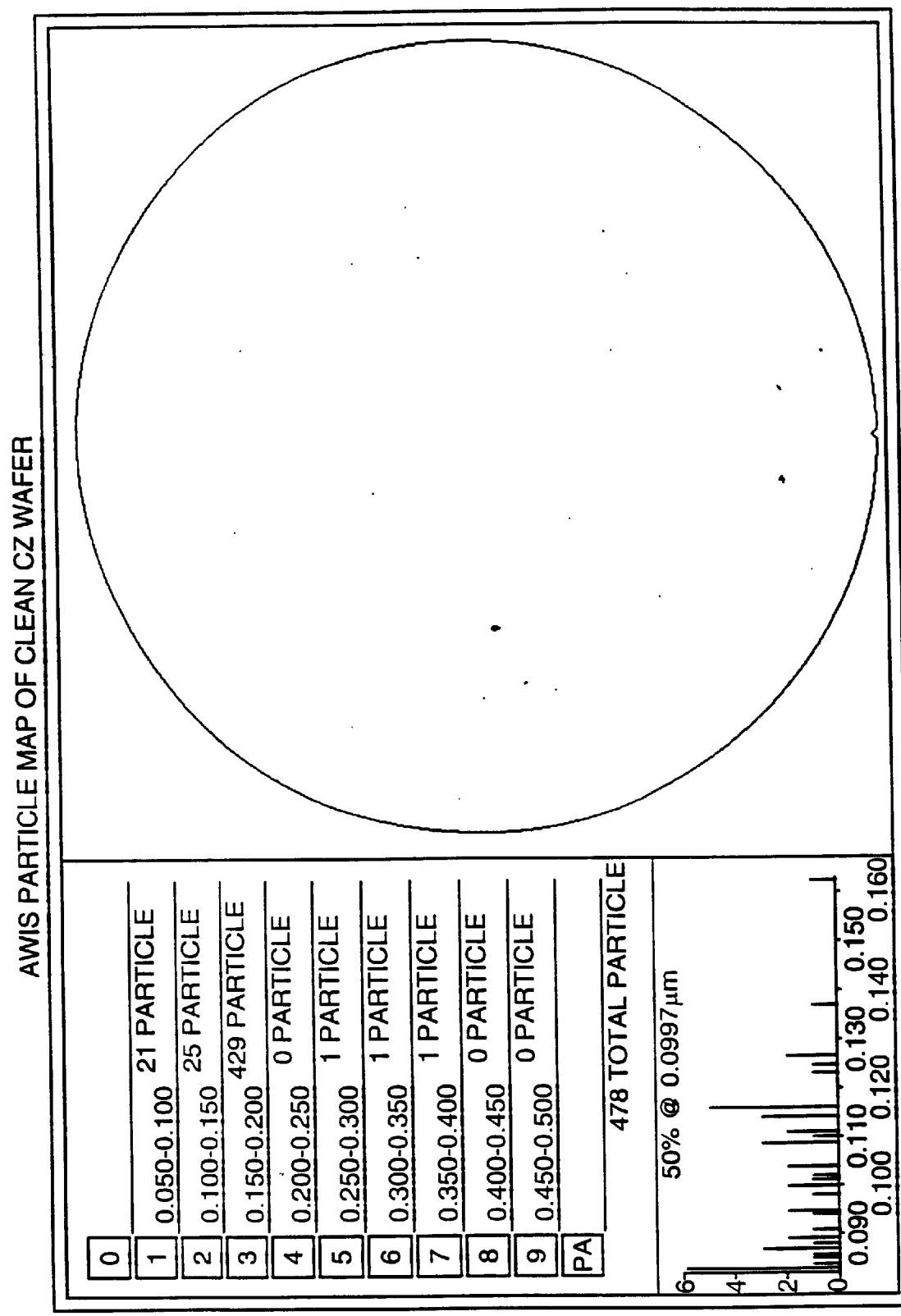
FIG. 19 is a particle map of a clean wafer.
Figure 20:
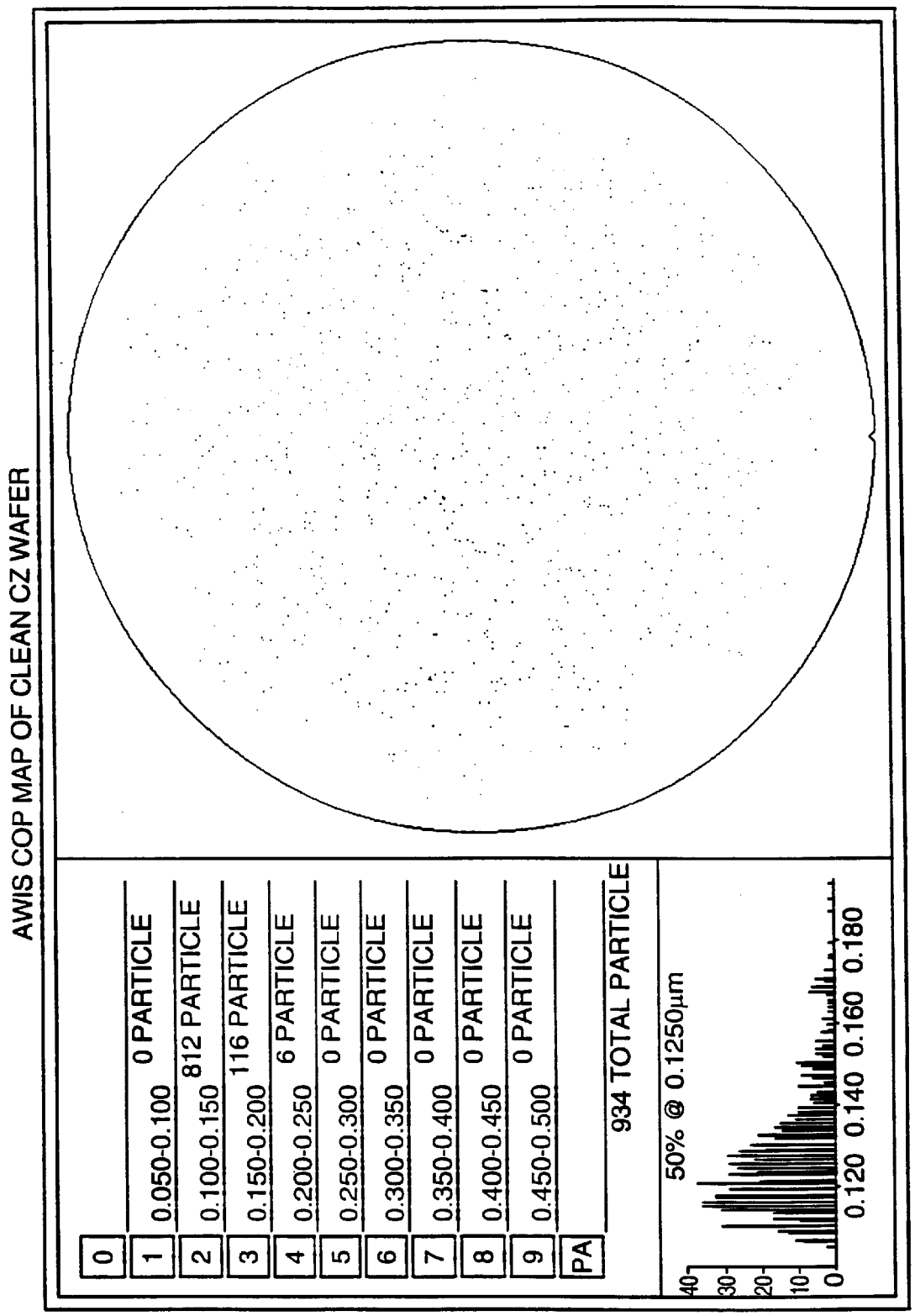
FIG. 20 is a COP map of a clean wafer.
Figure 21:
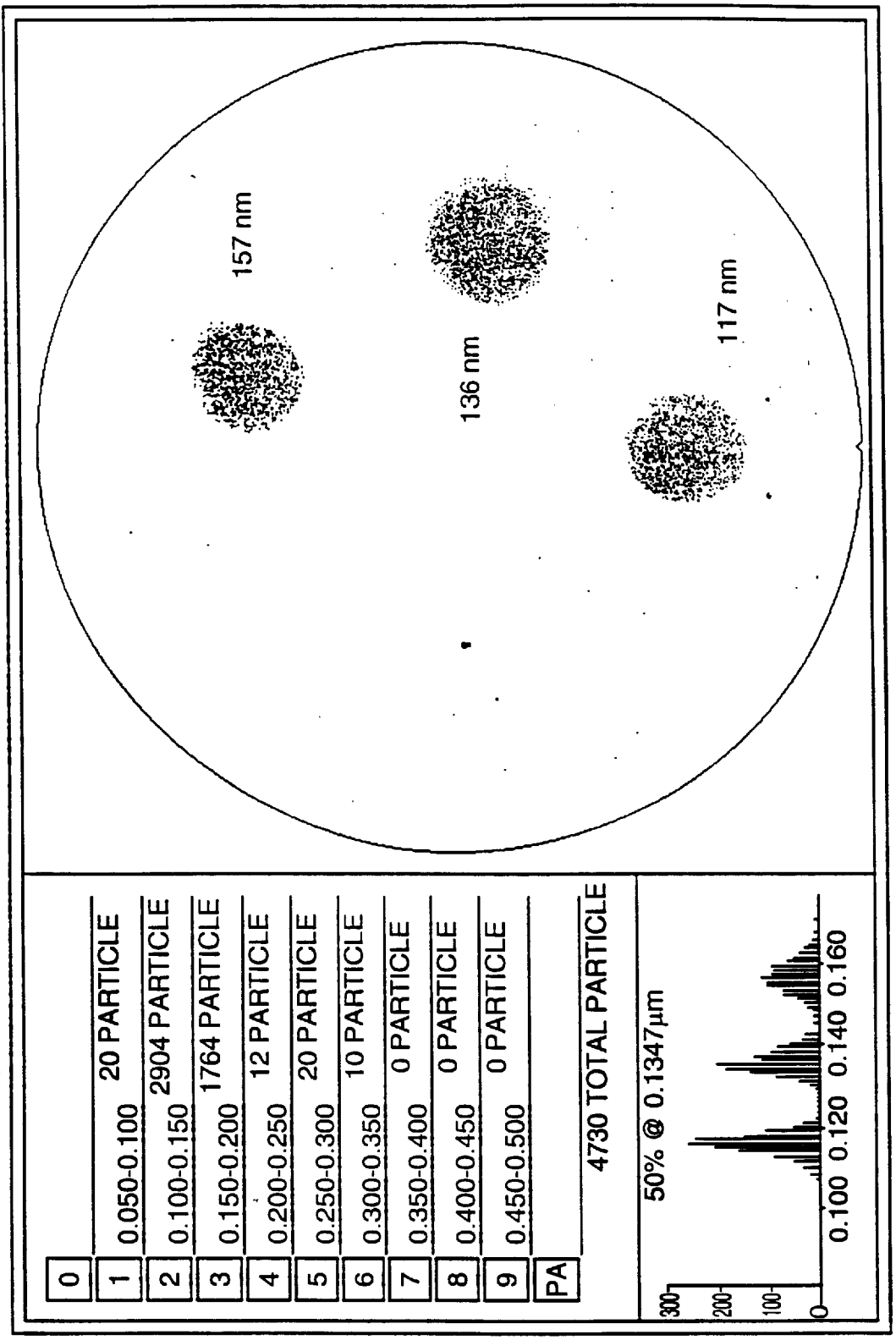
FIG. 21 is a particle map of the wafer of FIG. 19 after particle defects of known size have been deposited thereon.
Figure 22:
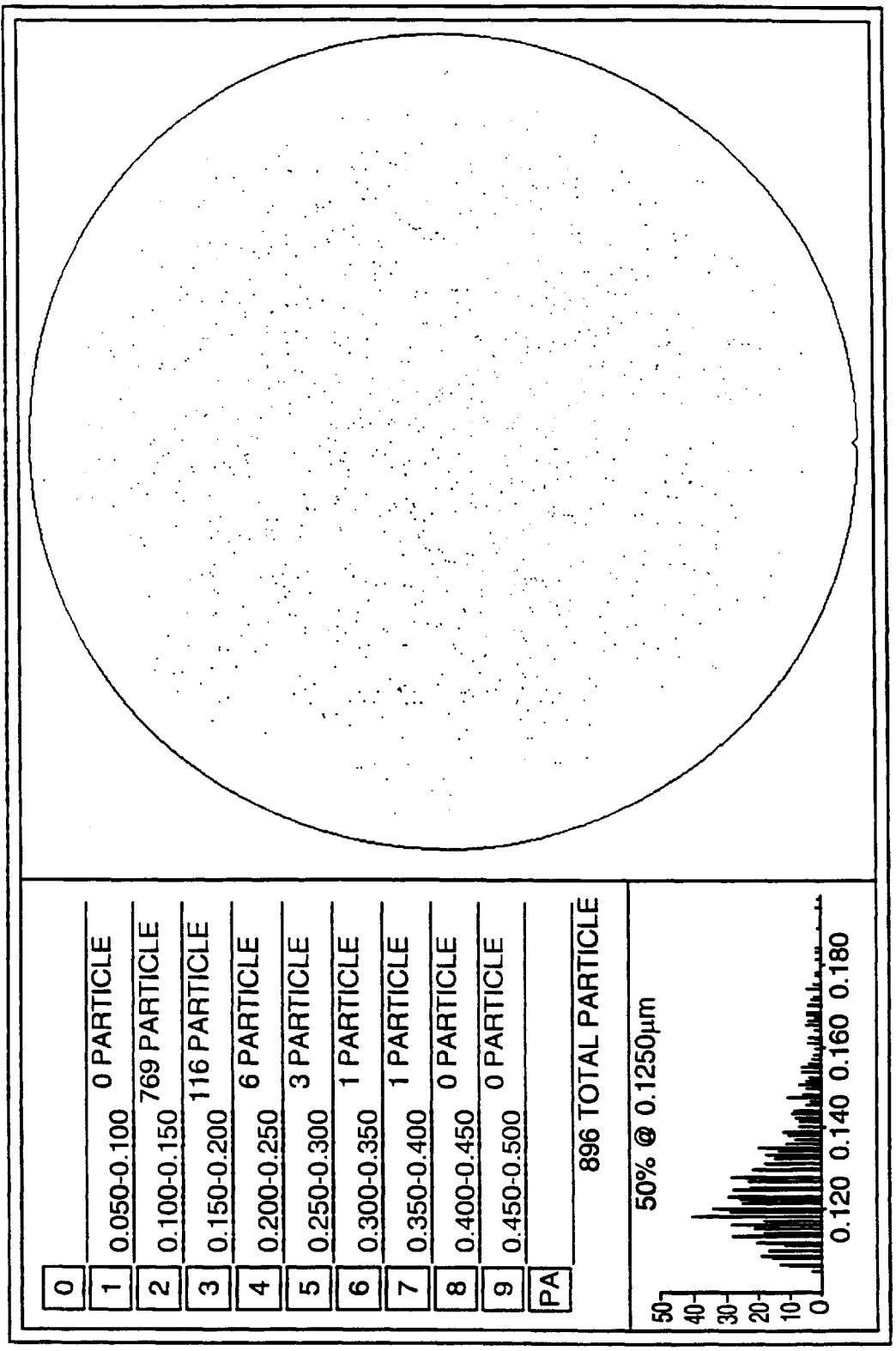
FIG. 22 is a COP map of the wafer of FIG. 21 with the particle deposition present, but not detected as COP defects.

During the scanning of a wafer, as signal events are thus classified into particle defects and pit defects, the resulting data may be stored in memory in a suitable format, such as a raster format, to define a "map" of the particles or pits on the surface of the wafer. In addition, the intensity values of the signal events, representing the indicated sizes of the particles or pits, may be stored to provide a histogram illustrating the size classifications of the defects. This information may be communicated to the user as a visual representation of the wafer on a video display. FIG. 19, for example, illustrates a video display which presents a particle map of a clean wafer, together with a histogram showing the distribution of particle sizes. FIG. 20 shows a map of the COPS or pits for the same wafer, and a size histogram for the pits. FIGS. 21 and 22 illustrate the sensitivity and selectivity of the apparatus and method of this invention. The same wafer which was used to produce the particle map of FIG. 19 was "seeded" with particle defects of known size in three regions on the wafer. FIG. 21 is a particle map of that wafer, and the three regions of seeded particles are clearly evident. FIG. 22 is a COP map of that same wafer. By comparing FIG. 20 (before seeding) with FIG. 22 (after seeding) it is evident that the COP map and the histogram are substantially unaffected by the heavy concentrations of seeded particles on the wafer.

In the drawings and specification, there have been disclosed typical preferred embodiments of the invention, and, although specific terms are employed, these terms are used in a descriptive sense only and not for purposes of limitation. The invention has been described in considerable detail with specific reference to various illustrated embodiments. It will be apparent, however, that various modifications and changes can be made within the spirit and scope of the invention as described in the foregoing specification and defined in the appended claims.

That which is claimed:

1. A surface inspection system for distinguishing between particle defects and pit defects on a surface of a workpiece comprising:

an inspection station for receiving the workpiece;

a scanner positioned to scan a surface of the workpiece at the inspection station, the scanner including a light source arranged to project p-polarized light at an angle of incidence oblique to the workpiece surface;

a first collector positioned to collect light scattered from the surface of the workpiece at a central zone;

a second collector positioned to collect light scattered from the surface of the workpiece at an oblique zone offset angularly from the central zone;

one or more converters for converting the collected light components into respective signals representative of the light scattered into the central zone and oblique zone; and a system controller configured to receive the signals, compare the signals, and classify defects as pits or particles based at least in part on the comparison.

2. The surface inspection station of claim 1 wherein the central zone includes a scattering direction substantially perpendicular to the surface.

3. The surface inspection station of claim 1 wherein the oblique zone is offset at least forwardly of the central zone.

4. The surface inspection station of claim 3 wherein the oblique zone receives substantially only forward scattered light.

5. The surface inspection system of claim 1 wherein the oblique zone is offset at least backwardly of the central zone.

6. The surface inspection system of claim 5 wherein the oblique zone receives substantially only backscattered light.

7. The surface inspection system of claims 1, 2, 3, 4, 5 or 6 wherein the system controller compares the ratio of the signals to a predetermined value.

8. The surface inspection system of claim 7 wherein the collected light components are converted into respective intensity signals representative of the intensity of the light scattered into the central zone and oblique zone and the system controller classifies a defect as a particle if the ratio of the intensity signal from the oblique zone to the intensity signal from the central zone exceeds a threshold value.

9. The surface inspection system of claim 7 wherein the collected light components are converted into respective intensity signals representative of the intensity of the light scattered into the central zone and oblique zone and the system controller classifies a defect as a pit if the ratio of the intensity signal from the central zone to the intensity signal from the oblique zone exceeds a predetermined measure.

10. The surface inspection system of claims 1, 2, 3, 4, 5 or 6 wherein the collected light components are converted into respective intensity signals representative of the intensity of the light scattered into the central zone and oblique zone, and the system controller classifies a defect as a particle if the intensity signal from the oblique zone exceeds the intensity signal from the central zone by a predetermined value.

11. The surface inspection station of claim 1 wherein the oblique zone receives substantially only backscattered light, and the surface inspection station further comprises a third collector positioned to collect light scattered from the surface of the workpiece at a second oblique zone offset angularly from said central zone, wherein the second oblique zone receives substantially only forward scattered light.

12. The surface inspection station of claim 11 wherein the collected light components are converted into respective intensity signals representative of the intensity of the light scattered into the central zone and oblique zone, and the system controller compares the intensity signal from each zone and classifies a defect as a particle if the intensity signal from either of the oblique zones exceeds the intensity signal from the central zone by a predetermined value.

13. The surface inspection system of claim 1 wherein the system controller further counts the number of defects classified as pits.

14. The surface inspection system of claim 1 wherein the system controller further counts the number of defects classified as particles.

15. The surface inspection system of claim 1 wherein the system controller further determines the size of the pits and particles detected on the surface of the workpiece.

16. The surface inspection system of claim 15 wherein the system controller further groups the pits and particles based at least in part on the determination of size.

17. The surface inspection system of claim 16 wherein the system controller further counts the number of pits and particles in each size group.

18. The surface inspection system of claim 1 wherein the system controller further produces a map of the pits and particles on the surface of the workpiece.

19. The surface inspection system of claim 1 wherein the system controller further sorts the workpieces based at least in part on whether the system controller classifies a defect as a pit or a particle.

20. The surface inspection system of claim 19 wherein the system controller sorts the workpieces for recleaning based at least in part on whether the system controller classifies a defect as a pit or a particle.

21. A surface inspection system for distinguishing between particle defects and pit defects on a surface of a workpiece comprising:
  an inspection station for receiving the workpiece;
  a scanner positioned to scan a surface of the workpiece at the inspection station, the scanner including a light source arranged to project p-polarized light at an angle of incidence oblique to the workpiece surface;
  a first collector positioned to collect light scattered from the surface of the workpiece at a central zone;
  a second collector positioned to collect light scattered from the surface of the workpiece at an oblique zone offset angularly from the central zone;
  one or more converters for converting the collected light components into respective signals representative of the light scattered into the central and oblique zones;
  a comparator configured to receive and compare the signals; and
  a classifier configured to classify defects as pits or particles based at least in part on the comparison by the comparator.

22. The surface inspection system of claim 21 wherein the comparator compares the ratio of the signals to a predetermined value.

23. The surface inspection system of claim 22 wherein the collected light components are converted into respective intensity signals representative of the intensity of the light scattered into the central zone and oblique zone, and the classifier classifies a defect as a particle if the ratio of the intensity signal from the oblique zone to the intensity signal from the central zone exceeds a threshold value.

24. The surface inspection system of claim 22 wherein the collected light components are converted into respective intensity signals repressentative of the intensity of the light scattered into the central zone and oblique zone, and the classifier classifies a defect as a pit if the ratio of the intensity signal from the central zone to the intensity signal from the oblique zone exceeds a predetermined measure.

25. A surface inspection system for distinguishing between particle defects and pit defects on a surface of a workpiece comprising:
  an inspection station for receiving the workpiece;
  a scanner positioned to scan a surface of the workpiece at the inspection station, the scanner including a light source arranged to project p-polarized light at an angle of incidence oblique to the workpiece surface;
  a first collector positioned to collect light scattered from the surface of the workpiece at a central zone;
  a second collector positioned to collect light scattered from the surface of the workpiece at an oblique zone offset angularly from the central zone;
  one or more converters for converting the collected light components into respective signals representative of the light scattered into the central and oblique zones;
  a system controller configured to receive the signals, compare the signals, classify defects as pits or particles based at least in part on the comparison, and produce a map of the pits and particles on the surface of the workpiece.

26. The surface inspection system of claim 25 wherein the system controller produces a first map identifying the location of pit defects on the workpiece surface.

27. The surface inspection system of claim 26 wherein the system controller produces a second map identifying the location of particle defects on the workpiece surface.

28. The surface inspection system of claim 27 wherein the system controller further displays the first map and second map on a video display.

29. A surface inspection system for distinguishing between particle defects and pit defects on a surface of a workpiece comprising:
  an inspection station for receiving the workpiece;
  a scanner positioned to scan a surface of the workpiece at the inspection station, the scanner including a light source arranged to project p-polarized light at an angle of incidence oblique to the workpiece surface;
  a first collector positioned to collect light scattered from the surface of the workpiece at a central zone;
  a second collector positioned to collect light scattered from the surface of the workpiece at an oblique zone offset angularly from said central zone;

one or more converters for converting the collected light components into respective signals representative of the light scattered into said central and oblique zones;

a comparator comprising computer-readable medium which stores computer-executable instructions for distinguishing between particle defects and pit defects on the surface of the workpiece, the instructions causing the comparator to compare the signals and determine whether a defect is one of a pit or a particle based at least in part on the comparison.

30. A surface inspection system for distinguishing between particle defects and pit defects on a surface of a workpiece comprising:

an inspection station for receiving the workpiece;

a scanner positioned to scan a surface of the workpiece at the inspection station, the scanner including a light source arranged to project p-polarized light at an angle of incidence oblique to the workpiece surface;

a first collector positioned to collect light scattered from the surface of the workpiece at a central zone;

a second collector positioned to collect light scattered from the surface of the workpiece at an oblique zone offset angularly from said central zone;

one or more converters for converting the collected light components into respective signals representative of the light scattered into said central and oblique zones; and a system controller comprising computer-readable medium which stores computer-executable instructions for distinguishing between particle defects and pit defects on the surface of the workpiece, the instructions causing the system controller to compare the signals and classify defects as pits or particles based at least in part on the comparison.

31. The surface inspection system of claim 30 wherein the instructions cause the system controller to compare the ratio of the signals to a predetermined value.

32. The surface inspection system of claim 31 wherein the collected light components are converted into respective intensity signals representative of the intensity of the light scattered into the central zone and oblique zone, and the instructions cause the system controller to classify a defect as a particle if the ratio of the intensity signal from the oblique zone to the intensity signal from the central zone exceeds a threshold value.

33. The surface inspection system of claim 31 wherein the collected light components are converted into respective intensity signals representative of the intensity of the light scattered into the central zone and oblique zone, and the instructions cause the system controller to classify a defect as a pit if the ratio of the intensity signal from the central zone to the intensity signal from the oblique zone exceeds a predetermined measure.

34. The surface inspection system of claim 31 wherein the instructions further cause the system controller to produce a map of the pits and particles on the workpiece surface.

35. The surface inspection system of claim 34 wherein the instructions cause the system controller to produce a first map identifying the location of pit defects on the workpiece surface.

36. The surface inspection system of claim 35 wherein the instructions cause the system controller to produce a second map identifying the location of particle defects on the workpiece surface.

37. The surface inspection system of claim 36 wherein the instructions further cause the system controller to display the first map and second map on a video display.

38. The surface inspection system of claim 30 wherein the instructions further cause the system controller to count the number of defects classified as pits.

39. The surface inspection system of claim 30 wherein the instructions further cause the system controller to count the number of defects classified as particles.

40. The surface inspection system of claim 30 wherein the instructions further cause the system controller to determine the size of the pits and particles detected on the surface of the workpiece.

41. The surface inspection system of claim 40 wherein the instructions further cause the system controller to group the pits and particles based at least in part on the determination of size.

42. The surface inspection system of claim 41 wherein the instructions further cause the system controller to count the number of pits and particles in each size group.

* * * * *

UNITED STATES PATENT AND TRADEMARK OFFICE
CERTIFICATE OF CORRECTION

PATENT NO. : 6,292,259 B1  Page 1 of 1
DATED : September 18, 2001
INVENTOR(S) : Michael E. Fossey, John C. Stover and Lee D. Clementi It is certified that error appears in the above-identified patent and that said Letters Patent is hereby corrected as shown below:

<u>Title page,</u>
Item [75], Inventors, should read as follows:
-- Micheal E. Fossey; John C. Stover, both of Charlotte, NC (US);
  and Lee D. Clementi, of Lake Wylie, SC (US)

Signed and Sealed this

Eighteenth Day of June, 2002

Attest:

JAMES E. ROGAN
*Attesting Officer*  *Director of the United States Patent and Trademark Office*